United States Patent
Kaznessis et al.

(10) Patent No.: US 12,121,553 B2
(45) Date of Patent: Oct. 22, 2024

(54) COMPOSITIONS INCLUDING PROBIOTIC BACTERIA FOR THE EXPRESSION AND SECRETION OF ENTEROCINS TO CONTROL CLOSTRIDIA PERFRINGENS-INDUCED NECROTIC ENTERITIS IN LIVESTOCK AND RELATED METHODS

(71) Applicant: General Probiotics, Inc., St. Paul, MN (US)

(72) Inventors: Yiannis John Kaznessis, New Brighton, MN (US); Kathryn Gayle Kruziki, New Brighton, MN (US); Dimitrios Nikolaos Sidiropoulos, Minneapolis, MN (US)

(73) Assignee: General Probiotics, Inc., St. Paul, MN (US)

( * ) Notice: Subject to any disclaimer, the term of this patent is extended or adjusted under 35 U.S.C. 154(b) by 182 days.

(21) Appl. No.: 17/160,132

(22) Filed: Jan. 27, 2021

(65) Prior Publication Data
US 2021/0268034 A1 Sep. 2, 2021

Related U.S. Application Data

(60) Provisional application No. 62/966,354, filed on Jan. 27, 2020.

(51) Int. Cl.
*A61K 35/741* (2015.01)
*A23K 10/18* (2016.01)
(Continued)

(52) U.S. Cl.
CPC ............ *A61K 35/741* (2013.01); *A23K 10/18* (2016.05); *A23K 50/75* (2016.05); *A61K 38/164* (2013.01);
(Continued)

(58) Field of Classification Search
CPC ..... A61K 35/741; A61K 38/164; A61P 31/04; C07K 14/315; A23K 50/75; C12N 15/70; C12N 1/205
See application file for complete search history.

(56) References Cited

U.S. PATENT DOCUMENTS

| 7,754,469 B2 | 7/2010 | Baltzley et al. |
| 9,050,281 B2 | 6/2015 | Lang et al. |

(Continued)

FOREIGN PATENT DOCUMENTS

| WO | 2007025333 | 3/2007 | |
| WO | WO-2007025333 A1 * | 3/2007 | ......... A61K 39/0258 |

(Continued)

OTHER PUBLICATIONS

McClure. "Mechanism and Control of Transcription Initiation in Prokaryotes", 1985, Annual Reviews Biochemistry, vol. 54, p. 171-204. (Year: 1985).*

(Continued)

*Primary Examiner* — Gary B Nickol
*Assistant Examiner* — Amelia Nicole Dickens
(74) *Attorney, Agent, or Firm* — Pauly, DeVries Smith & Deffner LLC

(57) ABSTRACT

This invention relates, at least in part, to engineered antimicrobial probiotics for the prevention or treatment of *Clostridia perfringens*-induced necrotic enteritis in animals and related methods. In an embodiment, a composition for treatment of chickens is included. The composition can include a bacterium originally isolated from the small intestinal tract of healthy chickens and can be genetically engineered with two exogenous polynucleotides. A first exogenous polynucleotide can include a heterologous promoter and a polynucleotide that encodes an antimicrobial protein. A second exogenous polynucleotide can include a heterolo- (Continued)

Figure 1:
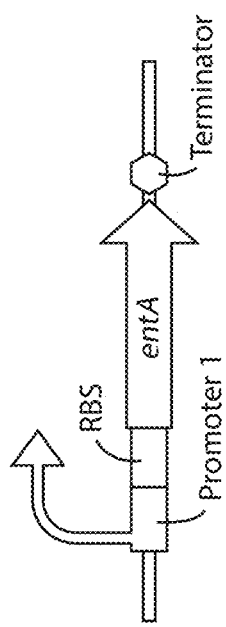

gous promoter and a polynucleotide that encodes proteins that function to secrete the antimicrobial protein to the extracellular environment. In an embodiment, the antimicrobial peptide can be effective in killing *C. perf.* inside the gastrointestinal tract of chickens.

13 Claims, 7 Drawing Sheets

Specification includes a Sequence Listing.

(51) Int. Cl.
 &nb

COMPOSITIONS INCLUDING PROBIOTIC BACTERIA FOR THE EXPRESSION AND SECRETION OF ENTEROCINS TO CONTROL CLOSTRIDIA PERFRINGENS-INDUCED NECROTIC ENTERITIS IN LIVESTOCK AND RELATED METHODS

This application claims the benefit of U.S. Provisional Application No. 62/966,354, filed Jan. 27, 2020, the content of which is herein incorporated by reference in its entirety.

REFERENCE TO SEQUENCE LISTING

This application is being filed electronically via EFS-Web and includes an electronically submitted sequence listing in .txt format. The .txt file contains a sequence listing titled "269-0002USU1-SEQS_ST25-replacement.txt" created on May 18, 2021 and having a size of 38 KB. The sequence listing contained in this .txt file is part of the specification and is incorporated herein by reference in its entirety.

FIELD

This disclosure relates to antimicrobial probiotics which may be used, for example, to control *Clostridia perfringens* (*C. perf*) and necrotic enteritis in livestock. Embodiments herein relate to the use of engineered antimicrobial probiotics to improve animal health and well-being. Embodiments herein relate to the improvement of the safety and quality of end products derived from animals. More specifically, some embodiments relate to new probiotic bacteria isolated from natural environments and to the genetic engineering and/or screening of the isolated probiotic bacteria for the treatment of *C. perf.* infections in pre-harvest broilers.

BACKGROUND

Pressures on Global Meat Production

Global food production is predicted to need to double in the next few decades, to meet the demand by earth's population, which is projected to reach nearly 10 billion by 2050. This demand along with a confluence of environmental factors, including water scarcity and climate instabilities, are exerting pressure on global food security (FAO (*Food and Agriculture Organization of the United Nations*). 2017. *The future of food and agriculture: Trends and challenges*. Available at http: www.fao.org 3 a-i6583e.pdf).

Due to the growing human population and historically high standards of living, there is a substantial increase in demand for animal protein diets. Global demand for beef, pork and chicken has nearly tripled in the past three decades and although there is pressure to reduce beef production for environmental reasons, pork and poultry production is projected to nearly double again in the following three decades.

The U.S. National Academy of Sciences concludes in a recent report "Science Breakthroughs to Advance Food and Agricultural Research by 2030" that "Today, the U.S. food and agricultural enterprise faces formidable challenges that will test its long-term sustainability, competitiveness, and resilience" (*National Academies of Sciences, Engineering, and Medicine.* 2018. *Science Breakthroughs to Advance Food and Agricultural Research* by 2030. *Washington, DC: The National Academies Press*. doi: https: doi.org 10.17226/25059).

Science-based improvements have historically enabled agriculture to produce food for a growing population. For decades, antibiotics have helped producers raise healthy livestock. Antibiotics have also often been used to promote growth and improve feed efficiency, even in the absence of infection (*White W. Medical Consequences of Antibiotic Use in Agriculture, Science,* 1998, 279, 996). Arguably, antibiotics have facilitated and sustained, along with major advances in animal breeding and in production, major livestock productivity increases.

Use of Antibiotics in Livestock Production

Of growing concern is the continuing emergence of microbial resistance to first line antibiotics (*US CDC, Antibiotic Resistance Threats in the United States,* 2013. Available at https: www.cdc.gov drugresistancelpdflar-threats-2013-508.pdf). It is estimated that over 1 million people are sickened in the US by multidrug-resistant infections and over 20,000 die every year. The trends of increasingly frequent multidrug-resistant pathogens are disconcerting. In January 2017, the U.S. Center for Disease Control announced the death of a woman in Nevada by a bacterial strain that is pan-resistant, i.e. resistant to all antibiotics available in the U.S.

One possible source of drug-resistance emergence is the widespread use of antibiotics in farm animal production (*US FDA,* 2016 *Summary Report on Antimicrobials Sold or Distributed for Use in Food-Producing Animals*. Available at https: www.fda.gov downloads/forindustry userfees animaldruguserfeeactadufa ucm588 085.pdf). An estimated 14,000 tons of antibiotics, or approximately 70% of all antibiotics produced in the U.S., were administered to cattle, pigs and poultry in 2015.

Alarmingly, there has been substantial overlap between classes of antibiotics listed as critically important for human health by the World Health Organization and those antibiotics listed as critically important in agriculture by the World Organization for Animal Health (*Joint FAO/WHO OIE Expert Meeting on Critically Important Antimicrobials*, Rome, Italy, Nov 2007, http: www.who.intfoodborne_disease/resources/Report_CIA_Meeting.pdf). For example, three classes of antibiotics; quinolones, 3rd and 4th generation cephalosporins, and macrolides, were reportedly used in agriculture, even though they are among the few viable therapeutic solutions against certain serious infections in humans.

The precise contribution of antibiotics used in livestock to human infections by antibiotic-resistant microbes is under debate (*Editorial, Safety from farm to fork, Nature Reviews Microbiology,* 2009, 7, 478). In complex systems such as food production, it is indeed difficult to establish causal relationships between the use of antibiotics in animal feed and gastrointestinal infections where antibiotic-resistant microbes affect human populations. Nevertheless, there is evidence that transmission of resistant strains to humans does occur through food (McEwen S A, Fedorka-Cray P J. *Antimicrobial use and resistance in animals. Clin Infect Dis* 2002; 34:S93-S106).

Antibiotics in Livestock Production

Because of these concerns, the European Union banned the use of antibiotics in food animal production in 2006. Attempts were made to pass similar measures in the U.S. with legislation introduced in the House and the Senate, entitled the "Preservation of Antibiotics for Medical Treatment Act" (H.R. 965/S. 1211). The law would result in the "Phased Elimination of Nontherapeutic Use in Animals of Critical Antimicrobial Animal Drugs Important for Human Health".

The attempts to pass this law were met with resistance. There are, indeed, many important and demonstrated benefits of using antibiotics in livestock production. A widespread ban of antibiotics may then jeopardize the global supply of abundant, high-quality, nutritious, safe and relatively inexpensive food. In the U.S., a ban on the use of antibiotics, and in the absence of alternative antibiotic technologies, could result in substantially increased food prices (Karavolias, J. *Raised without antibiotics: impact on animal welfare and implications for food policy, Translational Animal Science,* 2(4), 2018, 337-348). This could diminish the enormous positive impact of the animal agriculture on the economy, estimated to $125 billion annually.

These negative effects notwithstanding, the FDA moved to curtail the use of medically important antibiotics for livestock production purposes. Drug companies have voluntarily adopted FDA Guidance #209 and Guidance #213, revising the FDA-approved labeled use conditions to remove the use of antimicrobial drugs for production purposes. The intent is to change the marketing status from over the counter to Veterinary Feed Directive (VFD) for antibiotics administered to animals.

With the VFD, beginning in 2017, over-the-counter antibiotics ceased being used in animal production. Antibiotics are now only prescribed for sick animals by licensed veterinarians. This step may help ensure judicious use of antibiotics. On the other hand, farmers now face the challenge of raising healthy animals without growth-promoting antibiotics.

*Clostridia Perfringens* and Necrotic Enteritis in Poultry

Focusing on the poultry industry, phasing out of antibiotics is already resulting in higher frequency of necrotic enteritis (NE). NE is a result of broiler intestinal damage usually occurring from *E. maxima* in the presence of a toxicogenic *C. perf.* strain. It is believed that coccidia weaken the mucus layer in the GI tract, enabling *C. perf.* to reach and destroy epithelial cells (Prescott, J. F., *The pathogenesis of necrotic enteritis in chickens: what we know and what we need to know: a review, Avian Pathology,* 45(3), 2016, 288-294).

NE causes a significant negative economic impact in broiler production. The acute form of NE leads to increased mortality in the broiler flocks, which can reach 1% losses per day for consecutive days. The subclinical form of NE manifests as damage to the intestinal mucosa, decreased nutrient uptake, and reduced weight gain. Estimates of $6 billion annually have been reported as the economic worldwide impact of NE on the global poultry industry.

*C. perf.* in poultry is also a significant risk for foodborne transmission to humans. Type A and type C *C. perf.* strains cause type A diarrhea and type C necrotic enteritis, respectively, in humans. Approximately 1 million cases of *C. perf.* infections are reported annually in the U.S.

Sustainable Production and Welfare of Livestock is at Risk

Sustainability adds another important dimension to consider as a result of phasing out antibiotics in livestock production. Numerous pathogens impact the health of animals and result in losses in animal production. Arguably, limiting the use of antibiotics may result in considerable losses of animals because of illness, substantial amounts of food lost, and, as a consequence, a significantly negative impact on the environment.

On a global scale, food worth $750 billion is lost or wasted each year throughout the entire supply chain, with approximately 25% of food being lost during production. According to a study by the UN Food and Agriculture Organization (FAO), food loss and waste accounts for about 3.3 giga-tones of greenhouse gas emissions.

It has been estimated that without antibiotics, 700 million additional birds will need to be raised to meet poultry demand in the U.S. annually, requiring approximately 2 billion additional gallons of water and 5.4 million additional tons of feed per year.

Another important dimension relates to the well-being of animals. Animals raised without antibiotics are much more likely to suffer from painful medical conditions. For example, poultry raised without antibiotics are more than three times as likely to experience ammonia burns in their eyes.

SUMMARY

Figure 4:
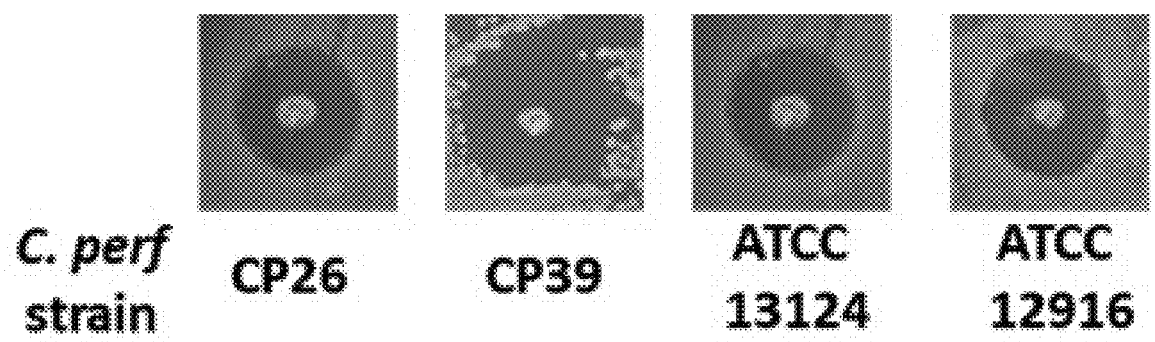

Embodiments herein relate to the isolation, characterization, screening, selection, and/or engineering of antimicrobial probiotics for the treatment of *C. perf.* and necrotic enteritis in animals. In an embodiment, a composition for treatment of chickens is included. In an embodiment, the composition is administered to chickens in water. In an embodiment, the composition can include a bacterium originally isolated from the small intestinal tract of healthy chickens. In an embodiment, the bacterium can be tested for survival, growth, colonization, and metabolic activity in gastrointestinal tract environments. In an embodiment, the bacterium may be genetically engineered with two exogenous polynucleotides. A first exogenous polynucleotide can include a heterologous promoter and a polynucleotide that encodes an antimicrobial protein. A second exogenous polynucleotide can include a heterologous promoter and a polynucleotide that encodes proteins that function to secrete the antimicrobial protein to the extracellular environment. In an embodiment, the antimicrobial peptide can be effective in killing *C. perf.* inside the gastrointestinal tract of chickens.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures, in which:

FIG. 1 is a schematic diagram of the engineered Enterocin transcriptional unit including an assembled DNA sequence of a promoter, a ribosome binding site, enterocin A, and a transcription terminator site.

FIG. 2 is a schematic diagram of the secretion system transcriptional unit, including the genes cvaA and cvaB of the Microcin V secretion systems, the diagram specifically illustrating an assembled DNA sequence of a promoter, a ribosome binding site for cvaA, cvaA, a ribosome binding site for cvaB, and a transcription terminator site.

FIG. 3 is a schematic diagram of the plasmid map used to engineer cellbots for the expression of an antimicrobial peptide, the diagram specifically illustrating plasmid pKG00255 (SEQ ID No: 13) for the expression of an antimicrobial peptide (AMP) and the secretion machinery. The selection marker confers resistance to chloramphenicol.

FIG. 4 is a snapshot of stab-on-agar tests demonstrating antimicrobial activity of cellbot GP00837 (General Probiotics Inc. Accession Number 00837) against four different *C. perf.* strains. FIG. 4 specifically illustrates the activity of *E. coli* GP00837 constitutively expressing Enterocin A against four different *C. perf.* strains in an agar diffusion assay. The white dot at the center is the modified GP00837. The light background indicates *C. perf.* growth white the dark region is a zone of *C. perf.* growth-inhibition resulting from EntA secreted by GP00837.

Figure 5:
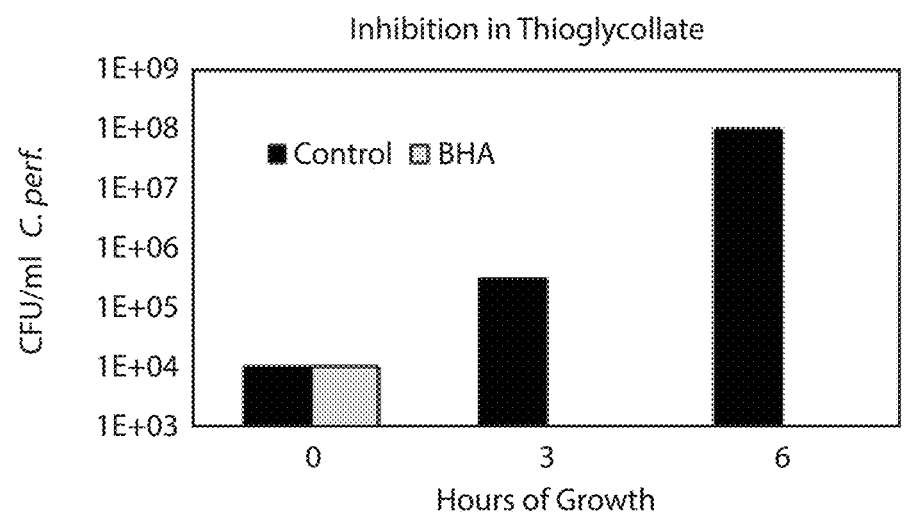

FIG. 5 is a graph of growth of *C. perf.* in rich media versus time showing how the supernatant containing antimicrobial peptides Enterocin B, Hiracin JM79 and Enterocin A inhibits the growth of the pathogen. Growth is measured at specific time points (0 hours, 3 hours, 6 hours, 24 hours) by plating and enumerating colony forming units (CFU) per ml. Growth is measured in the presence of supernatant from a culture of a cellbot producing Enterocin B, Hiracin JM79 and Enterocin A (BHA).

Figure 6A:
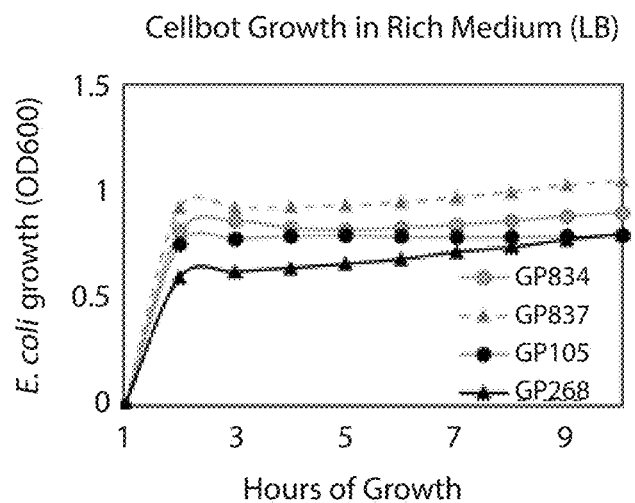
Figure 6B:
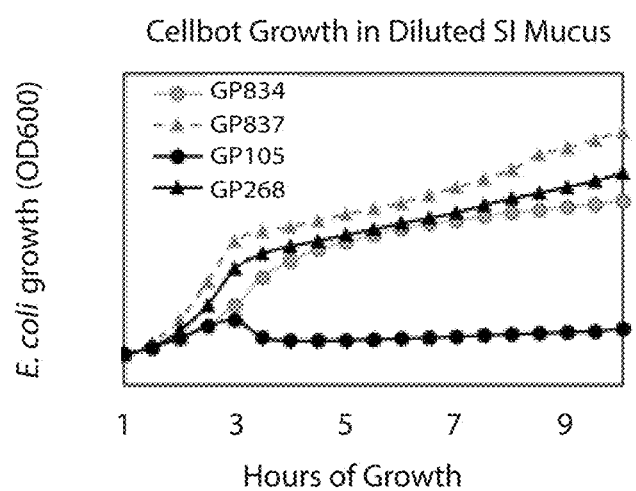

FIGS. 6A and 6B are graphs of growth of four cellbots versus time, demonstrating that cellbots grow variably in different environments. Growth is measured in terms of optical density at 600 nm. FIG. 6A shows growth in rich media and FIG. 6B shows growth in small intestinal mucus contents.

Figure 7A:
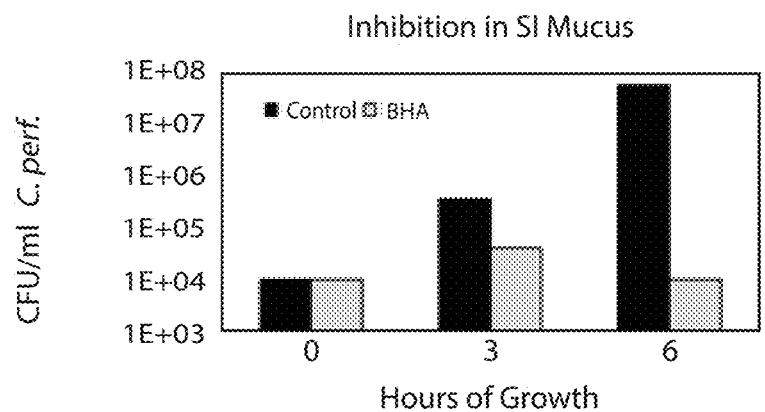
Figure 7B:
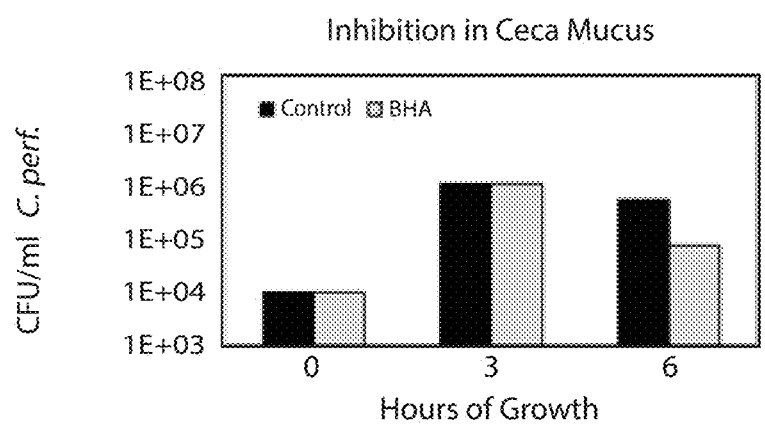

FIGS. 7A and 7B are graphs of growth of *C. perf.* versus time, showing how antimicrobial peptides inhibit the pathogen in various environments. Growth is measured at specific time points (0 hours, 3 hours, 6 hours, 24 hours) by plating and enumerating colony forming units (CFU) per ml. Growth is measured either with supernatant from a culture of a cellbot producing Enterocin B, Hiracin JM79 and Enterocin A (BHA), or from a culture of cellbot without an antimicrobial peptide. FIG. 7A shows growth in small intestinal contents. FIG. 7B shows growth in cecal mucus contents.

Figure 8:
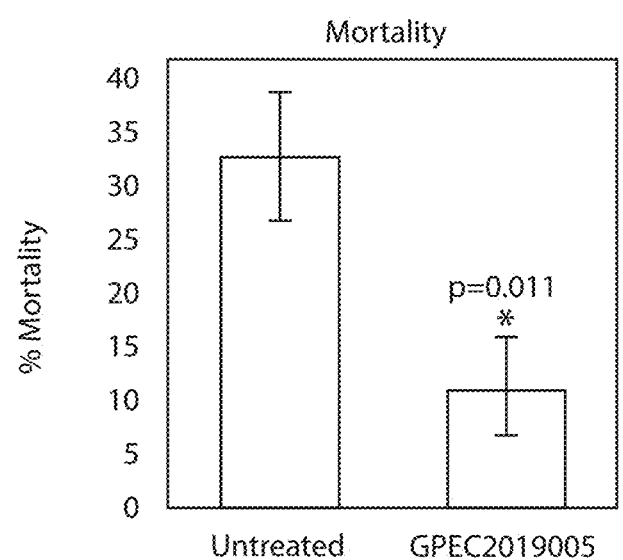

FIG. 8 is a graph demonstrating the lower mortality rate in birds challenged with *C. perf.* and necrotic enteritis treated with cellbot GP00837 (named GPEC2019005 in the animal study) compared to the mortality rate of untreated birds.

DETAILED DESCRIPTION

Probiotics or direct-fed microbials (DFMs) are considered a potential alternative to antibiotic feed additives to lower carriage of pathogens in livestock. The administration of DFMs is also purported to induce better nutrient digestion and enhance meat production in animals such as cattle and poultry. In addition, these products are thought to modulate the immune response of animals.

The FAO defines probiotics as "live micro-organisms that, when administered in adequate amounts, confer a health benefit on the host." A plethora of microbes are considered probiotics, including lactobacilli, bifidobacteria, bacilli and enterococci (FAO, Probiotics in Animal Nutrition, http: www.fao.org 3 a-i5933e.pdf).

An official list of microbes that can be marketed as generally regarded as safe (GRAS) DFMs is compiled by the Association of American Feed Control Officials (AAFCO). These DFMs are considered either as fermentation products or yeast products, and are accepted by the FDA as safe.

However, the performance and efficacy of probiotics have not been consistent. There are gaps in the understanding of probiotic organisms, especially in the context of the complex environment of the gastrointestinal tract. The modes of action of specific probiotics are generally not well understood. Competitive exclusion has been long believed to be an important mechanism of action, with probiotic organisms colonizing the gut and inhibiting pathogens from taking hold. Inhibition may occur simply as a result of limited resources, or more actively by the expression and secretion of inhibiting substances. More specifically probiotics are known to produce bacteriocins.

Bacteriocins are antimicrobial peptides (AMPs) produced by a wide range of bacteria. Unlike antibiotic peptides such as the gramicidins, polymyxins, or glycopeptides which are formed by multienzyme complexes, bacteriocins are ribosomally synthesized, i.e., their sequence is gene encoded. The exact biological role of many bacteriocins is still unknown but it is believed that bacteriocins have a vital role in ecology as they influence the composition of the microbial flora in certain growth habitats, e.g., the gastrointestinal tract of humans and animals (Nissen-Meyer, Ribosomally synthesized antimicrobial peptides: their function, structure, biogenesis, and mechanism of action Arch Microbiol. 1997, 167(2/3), 67-77 and references therein).

Numerous bacteriocins exert their antimicrobial effect by interfering with the cell membrane integrity of target bacteria, and they share several physicochemical features.

They are generally heat-stable, small in size, often cationic and have amphiphilic or hydrophobic structure.

However, they differ greatly from eukaryotic AMPs which often serve as the first line of defense against invading pathogens in mammals: bacteriocins can be very potent and may be able to act at pico- to nanomolar concentrations, whereas micromolar concentrations are often required for the activity of eukaryotic AMPs. Most bacteriocins also have a somewhat narrow target spectrum; individual bacteriocins are usually active against just few species or genera. In contrast, eukaryotic AMPs as well as traditional antibiotics are generally less specific, targeting a large diversity of different bacteria.

Consequently, in terms of potency and specificity, bacteriocins may be superior to traditional antibiotics and eukaryotic AMPs.

Bacteriocins can thus be very useful in therapeutic treatments where a particular pathogen is to be removed from a complex multi-species environment (such as in the gut) without causing adverse secondary effects as normally occur with common antibiotics.

For all the promise of bacteriocins, in particular, and antimicrobial peptides, in general, a critical barrier in using these compounds as therapeutics exists. It is difficult to administer AMPs orally or intravenously for therapeutic purposes. As proteins they are quickly degraded, and in high initial dosages they may become toxic to host cells. A technology that could safely deliver bacteriocins at the site of infection, such as inside the GI tract of animals, would be advantageous.

Described herein is the development of engineered antimicrobial probiotics, "cellbots" for short, which affect the viability of *C. perf.* in the GI tract of livestock. The desired outcome is a cellbot that can safely and effectively reduce the amount of *C. perf.* in the gut. This may lower the risk of necrotic enteritis, morbidity and mortality, and lower the risk of production losses to livestock producers.

While not wishing to be bound by theory, it is believed that only certain specific natural isolates can be engineered to colonize the jejunum of chickens, be metabolically active inside the jejunum, express and secrete antimicrobial peptides that target *C. perf,* and/or reduce necrotic enteritis-induced morbidity and mortality in chickens.

"Effective" herein means measurably and consistently lowering *C. perf.* carriage inside the length of the GI tract of animals, and consequently lowering the incidence of necrotic enteritis and NE-induced animal morbidity and mortality.

"Safe" herein means the following risks are minimal: 1) the cellbot infects birds; 2) the cellbot negatively impacts the gastro-physiology of chicken; 3) the cellbot disrupts the normal gut microflora of chicken; 4) the cellbot has toxic effects; 5) the cellbot has immunogenic effects; 7) the cellbot cannot be contained and spreads to the environment.

Methods are presented for the following primary performance criteria to be met for a safe, therapeutic effect against *C. perf.*
1. The cellbot survives the path to the GI tract through the stomach
2. The cellbot colonizes the gut in the vicinity of the pathogen
3. The cellbot is metabolically active inside the gut
4. The cellbot expresses and secretes antimicrobial proteins
5. The antimicrobial proteins are stable inside the gut
6. The antimicrobials proteins preferentially and effectively kill the pathogen
7. There are no adverse effects on the host Herein we describe an iterative method for all the primary performance criteria to be met. To our knowledge it is challenging to make a linear, reductionist approach work in engineering of cellbots. We can choose each component diligently, starting with the probiotic organism, and adding the synthetic DNA construct component by component, but the overall performance may not be sufficient inside the intestinal tract of an animal for an antimicrobial effect. We can measure the performance outcome, but when we change a different component, the outcomes observed with the first component may shift in unpredictable ways, hampering design efforts. For example, in rich media, overexpressing the secretion gene by using a strong constitutive promoter, predictably results in higher titer of secreted peptide. When this strong promoter is used in low pH or low nutrient environments the growth of the bacteria may be hampered, severely limiting the amount of peptide expressed and secreted.

In accordance with embodiments herein, linear development processes were replaced with iterative ones in the following four cycles:

Cycle 1. Build a Library of Organisms that can be Engineered into Cellbots.

The first cycle of the method consists of the following steps:

1. In various embodiments, a library of bacteria is isolated from a specific area of the intestinal tract of healthy animals, as described in Example 1 below. In various embodiments the intestinal location is the jejunum area. In other embodiments the intestinal location is the ileum or the cecum. In some embodiments the animals are infected with a pathogen. In some embodiments, the pathogen belongs to *Clostridia* spp., *Salmonella* spp., *Campylobacter* spp., Lawsonia spp., *Escherichia* spp., or *Streptococcus* spp.

In various embodiments, the isolated strains of bacteria are *E. coli*. In other embodiments, the isolated strains belong to *Bacillus* spp. *Lactobacillus* spp., and *Enterococcus* spp. In various embodiments isolates will re-colonize the area they have been isolated from upon administration to an animal. In various embodiments, the isolates will be metabolically active inside the intestinal tract of animals. For example, cellbots selected and engineered to target *C. perf.* must colonize the jejunum and be metabolically active in the jejunum because the jejunum is a main location of *C. perf.* colonization.

2. In various embodiments, the absence of virulence factors will be established with the experimental technique described in Example 2 below. In one embodiment, the absence of virulence factors associated with Avian Pathogenic *E. coli* (APEC) virulence will be established. In one embodiment, the absence of the following set of virulence factors will be established: cvaC, iroN, ompTp, hlyF, etsB, iss, aerJ/iutA, ireA, papC.

In various embodiments, antibiotic resistance markers will be absent. In some embodiments, the selected isolates will be susceptible to the following antibiotics, using the technique in Example 3 below: rifampicin, nalidixic acid, chloramphenicol, ampicillin, kanamycin, and spectinomycin.

In various embodiments, all isolated bacteria are characterized with the fingerprinting technique described in Example 4 below.

In various embodiments the serotype of the isolated bacteria will be determined with the method described in Example 5 below. In various embodiments, the serotype of selected isolated *E. coli* strains will not be of the following types: O26, O55, O103, O111, O121, O129abc, O145, O157, and O45.

In various embodiments, a library will be built with distinct isolates with no known virulence factors, toxins, and undesired resistance markers.

Cycle 2. Design DNA Sequences that Encode DNA Promoters, Antimicrobial Proteins and Secretion Genes.

3. Build/a library of DNA sequences, as described in Example 6 below, including DNA encoding for:
   a. antimicrobial peptides. In various embodiments DNA sequences will be assembled that encode for antimicrobial peptides that belong to the following classes: microcins, protegrins, ovispirins, and enterocins. In various embodiments DNA sequences will be assembled that encode for antimicrobial peptides that belong to the class of endolysins.

In various embodiments, the DNA sequence encodes for one of the following set of antimicrobial peptides: Enterocin A, Enterocin B, Enterocin P, Carnobacteriocin, Hiracin JM79, and Plantaricin EF, described in Table 3. In various embodiments, the DNA sequence encodes for two distinct antimicrobial peptides resulting in a polycistronic mRNA molecule. In various embodiments, the DNA sequence encodes for three distinct antimicrobial peptides, resulting in a polycistronic mRNA molecule. In various embodiments, the polycistronic DNA sequence encodes for two or three of the antimicrobial peptides in the following set: Enterocin A, Enterocin B, Enterocin P, Carnobacteriocin, Hiracin JM79, and Plantaricin EF.

b. DNA promoters. In various embodiments, DNA promoters are constitutive, stationary state, anaerobic state, and chloride-inducible DNA promoters. In various embodiments, DNA promoters are selected from the set of promoters described in Table 5.
   c. secretion genes. In various embodiments, secretion genes are genes of the Microcin V secretion system. In various embodiments, secretions genes are genes of the Microcin N secretion system. In various embodiments, secretion genes are genes of the Microcin C7 secretion system.
   d. Ribosome binding sites and termination sites. In one embodiment, the ribosome binding sites is the synthetic bicistronic design (SEQ ID No 11) as described by Mutalik (Mutalik V K, et al. Precise and reliable gene expression via standard transcription and translation initiation elements. Nat Methods. 2013, 10(4):354-360). In one embodiment, the termination site is the synthetic transcriptional terminator (SEQ ID No 12).
4. Assemble DNA constructs combining promoters, peptides and the secretion machinery. In one embodiment, a constitutive DNA promoter is operably linked to RBS sequence (SEQ ID No. 11) and to the DNA sequence encoding for Enterocin A which is linked to terminator site (SEQ ID No 12), followed by a constitutive promoter operably linked to RBS sequence and to the DNA encoding the secretion genes of the Microcin V system followed by termination site sequence (all contained in SEQ ID No 2).

The number of possible embodiments of distinct DNA sequences resulting by combining single peptide, promoters and secretion machinery is N=(M available peptides (times) P available promoters for the peptides (times) R available promoters for the secretion machinery (times) S distinct secretion gene sets).

The number of possible embodiments of distinct DNA sequences resulting by combining two distinct peptides, promoters and secretion machinery is N=((M available peptides choose 2) (times) P available promoters for the peptides (times) R available promoters for the secretion machinery (times) S distinct secretion gene sets).

The number of possible embodiments of distinct DNA sequences resulting by combining three distinct peptides, promoters and secretion machinery is N=((M available peptides choose 3) (times) P available promoters for the peptides (times) R available promoters for the secretion machinery (times) S distinct secretion gene sets).

5. Transform DNA constructs in library of I bacterial isolates selected in step 2. Select cellbots that contain the DNA plasmid. A maximum number of distinct embodiments of cellbots is the number of isolates times the number of distinct DNA sequences (C=I (times) N). In various embodiments, the transformation of DNA constructs in a library of isolates will be conducted as described in Example 7 below.

Cycle 3. Conduct Performance Tests and Select Best Performing Candidates.

6. Screen and rank-order systems against *C. perf.*

In one embodiment, the activity of a cellbot can be tested against *C. perf.* with a stab-on-agar test as described in Example 8 below.

In one embodiment, the activity of a cellbot can be tested against *C. perf.* with a supernatant test as described in Example 9 below. In one embodiment, the activity of a cellbot can be tested against an indicator strain with a liquid culture test as described in Example 9. In one embodiment, the indicator strain will be *Enterococcus* spp., as in Example 9.

7. Screen and rank-order systems for survival and growth in the following biomatrix assays:

a. stomach contents and low pH environments. In various embodiments, the experimental technique followed will be the one described in Example 10 below.

b. bile acid contents from the duodenum area. In various embodiments, the experimental technique followed will be the one described in Example 11 below.

c. mucus layer scraped from the jejunum, ileum and colon of animals. In various embodiments, the experimental technique followed will be the one described in Example 12.

8. Screen and rank-order systems for metabolic and antimicrobial activity in biomatrix assays. In various embodiments, experiments will be conducted to grow cellbots and *C. perf.* in these environments and measure the activity of peptides against *C. perf.* as described in Example 13 below. In various embodiments, experiments will be conducted to grow cellbots and an indicator strain in gut-mimicking environments and measure the activity of peptides against the indicator strain. In one embodiment, the indicator strain can be *Enterococcus faecium*. In one embodiment, the indicator strain can be *Enterococcus faecalis*.

9. Rank-order systems and select top cellbots to move into animal experiments. In various embodiments, the ranking and selecting of cellbots can be conducted as described in Example 14 below.

Cycle 4. Conduct Proof of Concept Animal Experiments.

In various embodiments, the animal experiments will be conducted with the experimental protocol described in Example 15 below.

Terms

As used herein, the term "protein" refers broadly to a polymer of two or more amino acids joined together by peptide bonds. The term "protein" also includes molecules which contain more than one protein joined by a disulfide bond, or complexes of proteins that are joined together, covalently or noncovalently, as multimers (e.g., dimers, trimers, tetramers). Thus, the terms peptide, oligopeptide, enzyme, subunit, and protein are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region," "coding sequence," and "open reading frame" are used interchangeably and refer to a nucleotide sequence that encodes a protein and, when placed under the control of appropriate regulatory sequences expresses the encoded protein. The boundaries of a coding region are generally determined by a translation start codon at its 5' end and a translation stop codon at its 3' end A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

As used herein, a "polycistronic mRNA" refers to a transcription product that includes two or more coding regions. Expression of the two or more coding regions is controlled by a single promoter, and the series of the two or more coding regions that are transcribed to produce a polycistronic mRNA is referred to as an operon.

As used herein, "genetically modified bacterium" refers to a bacterium which has been altered "by the hand of man." A genetically modified bacterium includes a bacterium into which has been introduced an exogenous polynucleotide, e.g., an expression vector.

As used herein, a "vector" is a nucleic acid (e.g., DNA) used as a vehicle to artificially carry genetic material (e.g., an engineered nucleic acid) into a cell where, for example, the nucleic acid can be replicated and/or expressed. A non-limiting example of a vector is a plasmid. Plasmids are double-stranded generally circular DNA sequences that are capable of automatically replicating in a host cell. Plasmids typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert.

As used herein, an "exogenous protein" and "exogenous polynucleotide" refers to a protein and polynucleotide, respectively, which is not normally or naturally found in a microbe, and/or has been introduced into a microbe. An exogenous polynucleotide may be separate from the genomic DNA of a cell (e.g., it may be a vector, such as a plasmid), or an exogenous polynucleotide may be integrated into the genomic DNA of a cell.

As used herein, a "heterologous" polynucleotide, such as a heterologous promoter, refers to a polynucleotide that is not normally or naturally found in nature operably linked to another polynucleotide, such as a coding region. As used herein, a "heterologous" protein or "heterologous" amino acids refers to amino acids that are not normally or naturally found in nature flanking an amino acid sequence.

As used herein, the term "variant" refers to a polypeptide that comprises one or more differences in the amino acid sequence of the variant relative to a reference sequence. For example, a "variant" polypeptide may include one or more deletions, additions or substitutions relative to a reference sequence. The term "variant" is not intended to limit the variant polypeptide to only those polypeptides made by the modification of an existing polypeptide or nucleic acid molecule encoding the reference sequence, but may include variant polypeptides that are made de novo or starting from a polypeptide other than the reference sequence.

As used herein, the term "conservative variant" shall refer to sequences which reflect the incorporation of conservative amino acid substitutions. Conservative substitution tables are well known in the art (see for example Creighton (1984) Proteins. W. 11. Freeman and Company (Eds) and Table 1 below).

TABLE 1

Examples of Conservative Amino Acid Substitutions

| Residue | Conservative Substitutions |
| --- | --- |
| Ala | Ser |
| Arg | Lys |
| Asn | Gln; His |

TABLE 1-continued

Examples of Conservative Amino Acid Substitutions

| Residue | Conservative Substitutions |
| --- | --- |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

As used herein, a protein may be "structurally similar" to a reference protein if the amino acid sequence of the protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein A candidate protein is the protein being compared to the reference protein. A candidate protein may be isolated, for example, from a microbe, or can be produced using recombinant techniques, or chemically or enzymatically synthesized Unless modified as otherwise described herein, a pair-wise comparison analysis of amino acid sequences can be carried out using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62, open gap penalty=11, extension gap penalty=1, gap x_dropoff-:50, expect=10, wordsize=3, and filter on. Alternatively, polypeptides may be compared using the BESTFIT algorithm in the GCG package (version 10.2, Madison Wis.).

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity-"and" similarity" can be readily calculated by known methods, including but not limited to those described in: *Computational Molecular Biology* (Lesk, A. M., ed.) Oxford University Press, New York (1988); *Biocomputing. Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., CABIOS. 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

Thus, as used herein, a candidate protein useful in the methods and compositions described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence.

Alternatively, as used herein, a candidate protein useful in the methods and compositions described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence Nucleic acids useful in the methods and compositions herein includes those with at least at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% nucleic acid sequence identity to the reference nucleic acid sequence.

Conditions that are "suitable" for an event to occur, such as expression of an exogenous polynucleotide in a cell to produce a protein, or production of a product, or "suitable" conditions are conditions that do not prevent such events from occurring. Thus, these conditions permit, enhance, facilitate, and/or are conducive to the event.

As used herein, an "animal" includes members of the class Mammalia and members of the class Ayes, such as human, avian, bovine, caprine, ovine, porcine, equine, canine, and feline.

As used herein, the recitations of numerical ranges by endpoints include all numbers subsumed within that range (e.g., 1 to 5 includes 1, 1.5, 2, 2.75, 3, 3.80, 4, 5, etc.).

As used herein, "probiotics" are "live microorganisms that, when administered in adequate amounts, confer a health benefit on the host", as defined by The Food and Agriculture Organization of the United Nations (FAO). A plethora of microbes are considered probiotics and can be used in an engineered state in accordance with embodiments herein, including *E. coli*. lactobacilli, bifidobacteria, bacilli and enterococci.

In accordance with embodiments herein, probiotic bacteria include bacteria discovered inside the gastrointestinal tract of animals.

As used herein, "cellbots" are probiotics that are modified using synthetic biology techniques to express and deliver antimicrobial proteins/peptides (including, but not limited to, bacteriocins). The present disclosure is based, at least in part, on unexpected findings showing that not all bacteria isolated from the gastrointestinal tract of animals can be engineered to re-colonize the gut of animals and maintain the metabolic activity for protein production. Methods are disclosed for isolating bacteria and for testing these isolated bacteria for their colonization and metabolic activity inside the gut. We find that only a small number of probiotic bacteria isolates can re-colonize the gut of animals and express and secrete antimicrobial peptides in suitable quantities to target pathogenic bacteria.

Although pathogens can be found throughout the GI tract, they also preferentially adhere to different parts of the GI tract. Clostridia spp. for example preferentially colonize the jejunum area of the small intestine of chickens. A probiotic organism genetically modified to target *C. perf* will perform better if it can colonize the jejunum and if it can be metabolically active and grow in the area of the jejunum. As discussed in Examples, only a small number of probiotic *E. coli* isolated from the jejunum area of the small intestine of chickens can re-colonize the jejunum and upon genetic modification express and secrete antimicrobial peptides.

Antimicrobial Peptides

As used herein, "antimicrobial peptides" are small proteins, typically between about 10 and about 100 amino acids in length that inhibit, and often kill, certain bacteria. As such, an antimicrobial peptide has antimicrobial activity that inhibits or kills a target microbe.

The target microbe may be a Gram-positive bacterium that is member of the genus *Clostridia*. Examples of Clostridia include, for instance, *Clostridia perfringens* and *Clostridia difficile*.

The target microbe may be in vitro or in vivo. For instance, in one embodiment, a target microbe may be one that is present in the gastrointestinal tract or urogenital system of a subject, and optionally may be pathogenic to the subject. For instance, in another embodiment, a target microbe may be one that is present in the ovaries of hens, contaminating the eggs inside the chicken before the shells are formed.

Whether an antimicrobial peptide has antimicrobial activity can be determined using different indicator strains. Examples of indicator strains include but are not limited to *Enterococcus* spp. and *Escherichia* spp. Examples of suitable indicator strains include, but are not limited to those listed in Table 2 below. In one embodiment, an indicator strain is a member of the genus *Enterococcus*, such as *E. faecalis* and *E. faecium*. Methods for testing the activity of an antimicrobial peptide include, but are not limited to, the stab-on-agar test as well as other methods useful for evaluating the activity of bacteriocins. Such methods are known in the an and are routine.

TABLE 2

Example indicator strains
Indicator strains

*Lactococcus lactis* subsp *lactis* IL1403
*Lactobacillus acidophilus* ATCC 4356
*Lactobacillus bulgaricus* ATCC 11842

TABLE 2-continued

Example indicator strains

| Indicator strains |
| --- |
| *Enterococcus faecalis* ATCC 700802 |
| *Enterococcus faecalis* ATCC 47077 |

An antimicrobial peptide may be naturally occurring or may be engineered. Antimicrobial peptides are produced by all classes of organisms, including mammals, bacteria, and phage. Examples of antimicrobial peptides are shown in Table 3.

TABLE 3

Exemplary antimicrobial peptides

| Antimicrobial Peptide | Amino Acid Sequence | Origin |
| --- | --- | --- |
| Enterocin A (EntA) | TTHSGKYYGNGVYCTKNK CTVDWAKATTCIAGMSIG GFLGGAIPGKC (SEQ ID NO: 14) | *E. faecium* (1) |
| Enterocin P (EntP) | ATRSYGNGVYCNNSKCW VNWGEAKENIAGIVISGW ASGLAGMGH (SEQ ID NO: 15) | *E. faecium* (2) |
| Enterocin B | ENDHRMPNELNRPNNLSK GGAKCGAAIAGGLFGIPKG PLAWAAGLANVYSKCN (SEQ ID NO: 16) | *E. faecium* (12) |
| Hiracin JM79 (HirJM79) | ATYYGNGLYCNKEKCWV DWNQAKGEIGKIIVNGWV NHGPWAPRR (SEQ ID NO: 17) | *E. hirae* (3) |
| Endolysin 170 (Lys170) | MAGEVFSSLITSVNPNPMN AGSRNGIPIDTIILHHNATT NKDVAMNTWLLGGGAGT SAHYECTPTEIIGCVGEQYS AFHAGGTGGIDVPKIANPN QRSIGIENVNSSGAPNWSV DPRTITNCARLVADICTRY GIPCDRQHVLGHNEVTAT ACPGGMDVDEVVRQAQQ FMAGGSNNAVKPEPSKPTP SKPSNNKNKEGVATMYCL YERPINSKTGVLEWNGDA WTVMFCNGVNCRRVSHPD EMKVIEDIYRKNNGKDIPF YSQKEWNKNAPWYNRLE TVCPVVGITKKS (SEQ ID NO: 18) | *E. faecalis* phage F170/08 (4) |
| PlyV12 | MSNINMETAIANMYALKA RGITYSMNYSRTGADGTG DCSGTVYDSLRKAGASDA GWVLNTDSMHSWLEKNG FKLIAQNKEWSAKRGDVVI FGKKGASGGSAGHVVIFIS STQIIHCTWKSATANGVYV DNEATTCPYSMGWYVYRL NGGSTPPKPNTKKVKVLK HATNWSPSSKGAKMASFV KGGTFEVKQQRPISYSYSN QEYLIVNKGTVLGWVLSQ DIEGGYGSDRVGGSKPKLP AGFTKEEATFINGNAPITTR KNKPSLSSQTATPLYPGQS VRYLGWKSAEGYIWIYAT DGRYIPVRPVGKEAWGTF KQDIEGGYGSDRVGGSKP KLPAGFTKEEATFINGNAPI TTRKNKPSLSSQTATPLYP GQSVRYLGWKSAEGYIWI YATDGRYIPVRPVGKEAW GTFK (SEQ ID NO: 19) | Encoded by phage F1 (5) |
| EFAL-1 | MKLKGILLSVVTTFGLLFG ATNVQAYEVNNEFNLQPW EGSQQLAYPNKIILHETAN PRATGRNEATYMKNNWF NAHTTAIVGDGGIVYKVAP EGNVSWGAGNANPYAPV QIELQHTNDPELFKANYKA YVDYTRDMGKKFGIPMTL DQGGSLWEKGVVSHQWV TDFVWGDHTDPYGYLAK MGISKAQLAHDLANGVSG NTATPTPKPDKPKPTQPSK PSNKKRFNYRVDGLEYVN GMWQIYNEHLGKIDFNWT ENGIPVEVVDKVNPATGQP TKDQVLKVGDYFNFQENS TGVVQEQTPYMGYTLSHV QLPNEFIWLFTDSKQALMY Q (SEQ ID NO: 20) | Produced by phage EFAP-1 (6) |
| ORF9 | MAGEVFSSLITSVNPNPMN AGSRNGIPIDTIILHHNATT NKDVAMNTWLLGGGAGT SAHYECTPTEIIGCVGEQYS AFHAGGTGGIDVPKIANPN QRSIGIENVNSSGAPNWSV DPRTITNCARLVADICTRY GIPCDRQHVLGHNEVTAT ACPGGMDVDEVVRQAQQ FMAGGSNNAVKPEPSKPTP SKPSNNKNKEGVATMYCL YERPINSKTGVLEWNGDA WTVMFCNGVNCRRVSHPD EMKVIEDIYRKNNGKDIPF YSQKEWNKNAPWYNRLE TVCPVVGITKKS (SEQ ID NO: 21) | From phage jEF24C (7) |
| Lys168 | MVKLNDVLSYVNGLVGK GVDADGWYGTQCMDLTV DVMQRFFGWRPYGNAIAL VDQPIPAGFQRIRTTSSTQI KAGDVMIWGLGYYAQYG HTHIATEDGRADGTFVSVD QNWINPSLEVGSPAAAIHH NMDGVWGVIRPPYEAESK PKPPAPKPDKPNLGQFKGD DDIMFIYYKKTKQGSTEQ WFVIGGKRIYLPTMTYVNE ANDLIKRYGGNTNVTTYN YDNFGLAMMEKAYPQVK L (SEQ ID NO: 22) | From phage F168/08 (8) |
| Plantaricin JK (PlnJK). Plantaricin JK is comprised of the two peptides Plantaricin J (PlnJ) and Plantaricin K (PlnK) | PlnJ GAWKNFWSSLRKGFYDGE AGRAIRR (SEQ ID NO: 23) PlnK RRSRKNGIGYAIGYAFGAV ERAVLGGSRDYNK (SEQ ID NO: 24) | Class IIb heterodimeric bacteriocin produced by *Lactobacillus plantarum* C11 (9) |

TABLE 3 -continued

Exemplary antimicrobial peptides

| Antimicrobial Peptide | Amino Acid Sequence | Origin |
|---|---|---|
| Plantaricin EF (PlnEF). Plantaricin EF is comprised of the two peptides Plantaricin E (PlnE) and Plantaricin F (PlnF) | PlnE FNRGGYNFGKSVRHVVDA IGSVAGIRGILKSIR (SEQ ID NO: 25) PlnF VFHAYSARGVRNNYKSAV GPADWVISAVRGFIHG (SEQ ID NO: 26) | Class IIb heterodimeric bacteriocin produced by *Lactobacillus plantarum* C11 (10) |
| Microcin N | AGDPLADPNSQIVRQIMSN AAWGAAFGARGGLGGMA VGAAGGVTQTVLQGAAA HMPVNVPIPKVPMGPSWN GSKG (SEQ ID NO: 27) | Produced by *E. coli* (11) |

Sources for Table 3. 1. Aymerich et al., 1996, Appl Environ Microbiol. 62:1676-1682Z 2. Cintas et al., 1997. Appl Environ Microbiol., 63:4321-4330: 3 Sánchez et al., 2007, FEMS Microbiol Lett. 270.227-236.4. Proemça et al., 2012. Microb Drug Resist., 18:322-332. 5. Fahmer et al., 1996, Chemistry & Biology 3:543-550; 5. Yoong et al., 2004, J. Bacteriol. 186.4808-4812; 6. Uchiyama et al., 2011. Appl Environ Microbiol. 77:580-585: 7 Son et al. 2010, J. Appl Microbiol. 108:1769-1779, 8. Proença et al., 2012, Microb Drug Resist. 9. Hauge et al. 1999, J Bacteriol., 181(3).740-7; 10. Zhang et al. Biochim Biophys Acta. 2016 Feb; 1858(2): 274-80. Corsimi et al., 2010. FEMS Microbiol Lett 312(2) 119-25. 12. Casaus et al., 1997, Microbiology. 143 (Pt 7):2287-94.

Examples of antimicrobial peptides also include those that are essentially identical to any one of the antimicrobial peptides in Table 3. As used herein, in the context of a protein "essentially identical" refers to a protein that differs from one of the proteins disclosed herein by 1, 2, 3, 4, 5, 6, 7, 8, 9, 10, 11, or 12 amino acid residues, but shares activity. For example, a protein that is essentially identical to an antimicrobial peptide differs from one of the antimicrobial peptides in in Table 3 at 1, 2, 3, 4, 5, 6, 7, 8, 9, 10, 11, or 12 amino acid residues and has antimicrobial activity. In one embodiment, the difference is a conservative substitution. Conservative amino acid substitutions are defined to result from exchange of amino acids residues from within one of the following classes of residues Class 1: Ala, Gly, Ser, Thr, and Pro (representing small aliphatic side chains and hydroxyl group side chains); Class 2: Cys, Ser, Thr, and Tyr (representing side chains including an —OH or —SH group); Class 3: Glu, Asp, Asn, and Gln (carboxyl group containing side chains): Class 4: His, Arg, and Lys (representing basic side chains); Class 5: Ile, Val, Leu, Phe, and Met (representing hydrophobic side chains); and Class 6: Phe, Trp, Tyr, and His (representing aromatic side chains).

Most bacteriocins also have a very narrow target spectrum; individual bacteriocins are active against a just few species or genera. On the contrary, eukaryotic AMPs as well as traditional antibiotics are generally much less specific, targeting a large diversity of different bacteria. Consequently, in terms of potency and specificity, bacteriocins may be superior to traditional antibiotics and eukaryotic AMPs. Bacteriocins can thus be very useful in therapeutic treatments where a particular pathogen is to be removed from a complex multi-species environment (such as in the gut) without causing adverse secondary effects as normally occur with common antibiotics.

Bacteriocins include class I and class II bacteriocins. An example of class II bacteriocins includes members of the subclass IIa bacteriocins. Class IIa bacteriocins are small (usually 37 to 48 amino acid), heat-stable, and non-post-translationally modified proteins that are typically positively charged and may contain an N-terminal consensus sequence-Tyr-Gly-Asn-Gly-(Val/Lys)-Xaa-Cys-(SEQ ID NO: 50). Examples of class IIa bacteriocins include, but are not limited to, those described in TABLE 5. Another example of class 11 bacteriocins includes members of the subclass IIb bacteriocins. Class IIb bacteriocins are heterodimeric bacteriocins that require two different molecules at approximately equal concentrations to exhibit optimal activity. Examples of class IIb bacteriocins include, but are not limited, to those described in TABLE 5

Another example of antimicrobial peptides includes endolysins. Endolysins are double-stranded DNA bacteriophage-encoded peptidoglycan hydrolases produced in phage-infected bacterial cells, and cause rapid lysis when applied to Gram-positive bacteria (Fenton et al., 2010. Bioeng Bugs. 1:9-16; Fischetti, 2008, Curr Opin Microbiol. 11:393-400).

A nucleotide sequence of a coding sequence encoding an antimicrobial peptide may be easily predicted based on reference to the standard genetic code. When an antimicrobial peptide is to be expressed in a particular microbe, a nucleotide sequence encoding the antimicrobial peptide may be produced with reference to preferred codon usage for the particular microbe.

A coding sequence encoding an antimicrobial peptide may further include nucleotides encoding a secretion signaling protein, such that the antimicrobial peptide and the secretion signaling protein are fused and expressed as a single protein. A secretion signaling protein targets a protein for secretion out of the cell, and is usually present at the amino-terminal end of a protein. Secretion signaling proteins useful in prokaryotic microbes are known in the art and routinely used. Examples of secretion signaling proteins useful in lactic acid bacteria, including *L. lactis*, Lb. *acidophilus*, Lb. *acidophilus*, Lb. *bulgaricus*, Lb. *reuteri*, and Lb. *plantarum* are known. One example of a useful secretion signaling protein is from the protein Usp45 (Van Asseldonk et al., 1990, Gene, 95, 155-160). Several variations on Usp45 have been explored and may also be employed (Ng and Sarkar, 2012, Appl. Environ. Microbiol., 79:347-356). Additionally, *lactobacillus* secretion tags including but not limited to Lp_3050 and Lp_2145 may be used in *L. lactis* and Lactobacilli spp.

In addition to the signal peptides mentioned above which rely on the general Sec secretion machinery, many antimicrobial peptides also have their own dedicated secretion machinery with corresponding secretion tags. These tags are typically associated with the antimicrobial peptide natively secreted by these transport systems, however, these tags can also be used to secrete non-native antimicrobial peptides. An example of this mechanism of secretion is a double-glycine-type leader, which has been used to secrete colicin V from *L. lactis*. In the majority of microcin transport systems, secretion systems are associated with self-immunity or proteolytic cleavage of the microcin precursor. The Class II microcin gene clusters often encode for a dedicated ABC transporter and an accessory protein.

In embodiments herein, genetically engineered bacteria can express and secrete one or more AMPs. In various embodiments herein, genetically engineered bacteria can express and secrete combinations of AMPs, such as two or more distinct AMPs.

Promoters and Sigma Factors

Naturally occurring bacteria monitor environmental conditions and they respond by modifying the expression pattern of their genes. Transcription of genes is carried out by a single species of RNA polymerase (RNAP). The core enzyme of RNAP executes RNA polymerization reactions, but it cannot recognize a DNA promoter, bind to it and initiate transcription. The task of promoter recognition in bacteria is left to one of a few protein subunits called sigma factors. Each sigma factor binds to its cognate promoter and connects with the RNAP core enzyme, forming the fully functioning RNAP holoenzyme. In *E. coli* there are seven known sigma factors and each bind to DNA promoters under different conditions. For example, Sigma 70 binds to its cognate DNA promoters at all times. Sigma 38 binds to its DNA cognate promoters in stationary state. Thus, expression of a gene of interest can be controlled by employing promoters that interact with sigma factors that are dominant under the desired expression condition. For example, by employing a promoter capable of binding sigma 38 but not sigma 70, gene expression would be upregulated in stationary phase rather than in exponential phase.

A complete list of known sigma factors in *E. coli* is presented in Table 4.

TABLE 4

Known Sigma Factors for *E. coli*

| Sigma factor | Gene | Purpose of Regulation |
| --- | --- | --- |
| $\sigma^{19}$ | FecI | Regulates iron transport. |
| $\sigma^{24}$ | RpoE | Extracytoplasmic/extreme heat stress. |
| $\sigma^{28}$ | RpoF | Flagellar control |
| $\sigma^{32}$ | RpoH | Heat shock. |
| $\sigma^{38}$ | RpoS | Starvation/stationary phase. |
| $\sigma^{54}$ | RpoN | Nitrogen-limitation. |
| $\sigma^{70}/\sigma^{A}$ | RpoD | "Housekeeping" or primary sigma factor. |

Source for Table 4. Gruber T M, Gross C A (2003). "Multiple sigma subunits and the partitioning of bacterial transcription space". Annual Review of Microbiology. 57: 441-66.

The sigma factors of *E. coli* are exemplified above. However, it will be appreciated that each bacterium may have different sigma factors.

Promoters used herein include but are not limited to, high, medium, and low expression constitutive promoters, promoters that respond to stress, nutrient limitations, varying PH, varying osmotic pressure, and promoters that activate in stationary state.

A list of example promoters is presented in Table 5.

TABLE 5

Examples of *E. coli* DNA promoters

| Promoter | Description | Source |
| --- | --- | --- |
| *Constitutive* | | |
| Anderson promoter library | Developed from library screen | 1 |
| P(Bla) | Ampicillin Resistance | 1 |
| P(Cat) | Chloramphenicol Resistance | 1 |
| P(Kat) | Kanamycin Resistance | 1 |
| Placl | lacI promoter | 2 |
| PlacZ | lacZ promoter | 1 |
| PlacIQ | mutated lacI promoter | 3 |
| LacUV5 | high expression lacZ promoter | 4 |
| GlnRS | glutaminyl-tRNA synthetase | 1 |
| T7 | Phage | 1 |
| SP6 | Phage | 1 |
| PN25 | Phage | 5 |
| *Exogenously-Induced* | | |
| PBAD | Arabinose-Inducible | 1 |
| Plac | Lactose-Inducible | 1 |
| PTac | Lactose-Inducible | 1 |
| PTet, PTetO, PTetA | Tetracycline-Inducible | 1 |
| PTrp | Tryptophan-Inducible | 1 |
| PCpxP | Glucose-Inducible | 6 |
| Pm or Psal | Salicylate-Inducible | 7 |
| *pH-Inducible* | | |
| PgadA | GadA promoter | 8 |
| PgadB | GadB promoter | 8 |
| PhdeA | HdeA promoter | 8 |
| *Osmotic Pressure/Salt-Induced* | | |
| PosmBp2 | OsmB promoter | 9 |
| Pgad | Chloride-Inducible promoter | 10 |
| PosmC | OsmC promoter | 11 |
| *Anaerobically-Induced* | | |
| PFnrS | small sRNA (FrnS) promoter | 12 |
| PynfEFG | YnfEFG operon promoter | 13 |
| pNirB | NirB promoter | 14 |
| ydfZ | YdfZ promoter | 13 |
| frdABCD | FrdABCD operon promoter | 13 |
| *Starvation-Induced* | | |
| osmBp2 | OsmB promoter | 9 |
| PmcjA | Microcin J25 mcjA native promoter | 15 |
| PmcjB | Microcin J25 mcjB native promoter | 15 |
| PmcjC | Microcin J25 mcjC native promoter | 15 |
| PyciG | YciG promoter | 16 |
| PkatE | KatE promoter | 16 |
| PgadA | GadA promoter | 16 |
| PosmY | OsmY promoter | 16 |
| *Temperature-Induced* | | |
| pTlpA | Induced at high temperatures | 17 |
| pR-pL | Induced at high temperatures | 18 |
| *Inflammation-Induced* | | |
| pYeaR | Nitrite/Nitrate-Inducible | 19 |
| pTTrBCA | Tetrathionate + Anaerobic (Inflammation) | 20 |
| *Quorum-Sensing* | | |
| pluxI and PlasI | Responds to AHL from Pseudomonas | 21 |
| PtpQrr4 | Responds to CAI-1 from Vibrio cholerae | 22 |

Sources for Table 5: 1. http://parts.igem.org/Promoters/Catalog/Ecoli/Constitutive; 2. Piraner D I, et al. Tunable thermal bioswitches for in vivo control of microbial therapeutics, Nat Chem Biol. 2017 Jan.; 13(1):75-80; 3. Suhyun K, et al. Quorum Sensing Can Be Repurposed To Promote Information Transfer between Bacteria in the Mammalian Gut, ACS Synth. Biol. 2018, 7, 9, 2270-2281; 4. Schlegel S, et al. Isolating *E. coli* strains for recombinant protein production, Cell Mol Life Sci. 2017 March; 74(5):891-908; 5. Kammerer W, et al. Functional dissection of *E. coli* promoters: information in the transcribed region is involved in late steps of the overall process, EMBO J. 1986 Nov.; 5(11): 2995-3000; 6. Courbet A, et al. Detection of pathological biomarkers in human clinical samples via amplifying genetic switches and logic gates, Sci Transl Med. 2015 May 27; 7(289):289ra83; 7. Royo J L, et al. In vivo gene regulation in *Salmonella* spp. by a salicylate-dependent control circuit, Nat Methods. 2007 Nov.:4(11): 937-42: 8. Tucker D L, et al. Gene Expression Profiling of the pH Response in *E. coli*, J. Bacteriol. 183: 6551-6558: 9. Boulanger A, et al. Multistress Regulation in *E. coli*: Expression of osmB Involves Two Independent Promoters Responding either to σS or to the RcsCDB His-Asp Phosphorelay, J Bacteriol. 2005 May:187(9):3282-6: 10. Sanders J W, et al. A chloride-inducible gene expression cassette and its use in induced lysis of *Lactococcus lactis*. Appl Environ Microbiol. 1997 Dec; 63(12): 4877-82.; 11. Gutierrez C, et al. Osmotic induction of gene osmC expression in E. coliK 12, J Mol Biol. 1991 Aug. 20:220(4): 959-73.: 12. Boysen A, et al. Translational Regulation of Gene Expression by an Anaerobically Induced Small Non-coding RNA in *E. coli*, J Biol Chem. 2010 Apr. 2:285(14): 10690-702: 13. Kang Y, et al. Genome-Wide Expression Analysis Indicates that FNR of *E. coli* K-12 Regulates a Large Number of Genes of Unknown Function, J Bacteriol. 2005 Feb: 187(3): 1135-1160; 14. Nasr R, et al. Construction of a Synthetically Engineered nirB Promoter for Expression of Recombinant Protein in *E. coli*, Jundishapur J Microbiol. 2014 Jul.; 7(7): e15942: 15. Chiuchiolo M J, et al. Growth-Phase-Dependent Expression of the Cyclopeptide Antibiotic Microcin J25, J Bacteriol. 2001 Mar: 183(5): 1755-1764: 16. Shimada T, et al. Classification and Strength Measurement of Stationary-Phase Promoters by Use of a Newly Developed Promoter Cloning Vector, J Bacteriol. 2004 Nov; 186(21):7112-22: 17. Hurme R, et al. A proteinaceous gene regulatory thermometer in *Salmonella*. Cell. 1997 Jul. 11:90(1):55-64.: 18. Valdez-Cruz N A, et al. Production of recombinant proteins in *E. coli* by the heat inducible expression system based on the phage lambda pL and/or pR promoters, Microb Cell Fact. 2010 Mar 19:9:18.: 19. Dobson R, et al. Characterization of a rationally engineered nitric oxide, nitrate and nitrite biosensor linked to a hybrid bacterial mammalian promoter, available online: https://doi.org/10.6084/m9.figshare.1103248.v1: 20. Kottula J W, et al. Programmable bacteria detect and record an environmental signal in the mammalian gut, PNAS Apr. 1, 2014 111 (13) 4838-4843: 21. Prindle A, et al. A sensing array of radically coupled genetic 'biopixels'. Nature. 2011:481:39-44.: 22. Jayaraman P, et al. Repurposing a Two-Component System-Based Biosensor for the Killing of *Vibrio* cholerac. ACS Synth Biol. 2017 Jul. 21:6(7): 1403-1415

In various embodiments, constitutive promoters J23100-109 (SEQ ID NOS: 3-5) perform best in nutrient-rich environments of the GI tract—their differences in strength of gene expression are also used as a way to produce antimicrobial peptides, maturation factors and secretion machinery at the most optimal ratios.

In various embodiments, the FNR promoter (SEQ ID NO: 6) acts as a constitutive control in the most anerobic environments of the GI tract, as it originates from a switch system in *E. coli* between aerobic and anaerobic metabolism, the FNR regulon.

In various embodiments, GadA/B promoters (SEQ ID NOS: 7-8) are pH sensitive, which makes them useful for the highly acidic components of the GI tract.

In various embodiments herein, rpoS promoters can be used. In various embodiments herein, anaerobically-inducible promoters can be used. In various embodiments herein, chloride-inducible promoters can be used. In various embodiments herein, stationary-phase promoters can be used.

In various embodiments, promoter osmB (SEQ ID NO: 9) is a stress-responsive rpoS promoter intended for nutrient-poor environments with a high salt/ion content (osmotic stress).

Compositions

In an embodiment, a composition for treatment of an animal is included. The composition can include a bacterium isolated from the intestinal tract of an animal and comprising an exogenous polynucleotide, the polynucleotide comprising a first heterologous promoter and a first polynucleotide that encodes an antimicrobial protein, wherein the first polynucleotide is operably linked to the first heterologous promoter. In various embodiments, the polynucleotide of the composition can further include a second heterologous promoter and a second polynucleotide that encodes suitable secretion genes, wherein the second polynucleotide is operably linked to the second heterologous promoter.

In some embodiments, the bacterium can include the *E. coli* strain GP00700 deposited under ATCC Accession No. PTA-126596. In some embodiments, the composition can further include a pharmaceutically acceptable carrier. In some embodiments, the bacterium can include the *E. coli* strain GP00695.

In some embodiments, the antimicrobial peptide has bacteriolytic or bacteriostatic activity against *Clostridia perfringens*. In some embodiments, the treated animal is a chicken. In some embodiments, the bacterium is isolated from the jejunum of healthy chickens. In some embodiments, the bacterium recolonizes the gastrointestinal tract of chicken infected with *Clostridia perfringens*. In some embodiments, the bacterium is metabolically active within the gastrointestinal tract of chicken.

In some embodiments, the first heterologous promoter and the second heterologous promoter are selected to respond to different sigma factors selected from the group consisting of σ70(RpoD), σ19 (FecI), σ24 (RpoE), σ28 (RpoF), σ32 (RpoH), 638 (RpoS), and σ54 (RpoN).

In some embodiments, the composition of any of claims 2-10, wherein the first heterologous promoter and the second heterologous promoter are selected to respond to different exogenous environmental conditions found in the gastrointestinal tract of animals, the exogenous environmental conditions defined by one or more of nutrient content, oxygen content, pH and bile concentration.

In some embodiments, at least one of the first heterologous promoter and the second heterologous promoter are selected from the group of constitutive promoters, exogenously-inducible promoters, pH-inducible promoters, osmotic pressure-inducible promoters, anaerobically-inducible promoters, starvation-inducible promoters, temperature-inducible promoters, inflammation-inducible promoters, and quorum-sensing promoters.

In some embodiments, the genetically engineered bacterium is a probiotic bacterium. In some embodiments, the genetically engineered bacterium is selected from the group consisting of *Bacillus, Bacteroides, Bifidobacterium, Escherichia, Lactobacillus*, and *Lactococcus*. In some embodiments, the genetically engineered bacterium is an *E. coli* strain that does not belong to the serotypes O26, O55, O103, O111, O121, O129abc, O145, O157, and O45. In some embodiments, the genetically engineered bacterium is an *E. coli* strain does not encode for Shiga toxin. In some embodiments, the genetically engineered bacterium is an *E. coli* strain that does not encode for the following virulence genes cvaC, iroN, ompTp, hlyF, etsB, iss, aerJ/iutA, ireA, papC. In some embodiments, the genetically engineered bacterium is an *E. coli* strain that is susceptible to the following antibiotics: rifampicin, nalidixic acid, chloramphenicol, ampicillin, kanamycin, and spectinomycin.

In some embodiments, the antimicrobial protein is selected from the group containing Enterocin A, Enterocin B, Enterocin P, Carnobacteriocin, Plantaricin EF, and Hiracin JM79, or conservative variants thereof.

In some embodiments, the heterologous promoters and the polynucleotides that encode the antimicrobial proteins are located on the chromosome of the bacterium. In some embodiments, the heterologous promoters and the polynucleotides that encode the antimicrobial proteins are located on a plasmid in the bacterium.

In some embodiments, the bacterium is isolated from the intestinal tract of a healthy animal.

In some embodiments, the exogenous polynucleotide that encodes an antimicrobial protein having at least 70, 80, 85, 90, 95, 98, 99, or 100% sequence identity with SEQ ID NO: 1.

In some embodiments, a pharmaceutically acceptable composition is included herein. The composition can include any of the aforementioned compositions. In some embodiments, a composition is formulated for oral administration. In some embodiments, a composition is formulated for incorporation in the water supply of the animal. In some embodiments, a composition is formulated for incorporation in the feed supply of the animal.

In some embodiments, a composition for treatment of an animal is included. The composition can include a bacterium isolated from the intestinal tract of an animal and transfected with a plasmid, the plasmid comprising an exogenous polynucleotide, the polynucleotide comprising a first heterologous promoter and a first polynucleotide that encodes an antimicrobial protein, wherein the first polynucleotide is operably linked to the first heterologous promoter.

In an embodiment, the plasmid can include at least about 70, 80, 85, 90, 92, 95, 98, 99 or 100% sequence identity with SEQ ID NO: 13, or a degree of sequence identity falling within a range between any of the foregoing.

SEQ ID No: 13 includes promoter J23100 (SEQ ID No. 5) at 77-111; DNA sequence of construct to express Enterocin A (SEQ ID No. 1—which itself includes SEQ ID No. 5 and SEQ ID No. 12) at positions 77-500; DNA sequence of synthetic transcriptional terminator (SEQ ID No. 12) at positions 372-500; and DNA sequence of construct to secrete Enterocin A (SEQ ID No. 2) at positions 513-4144.

Embodiments herein can specifically include a bacterium isolated from an intestinal tract of an animal comprising an exogenous polynucleotide including SEQ ID No. 1 (or a polynucleotide operative for expressing Enterocin A including at least about 70, 80, 85, 90, 92, 95, 98, 99 or 100% sequence identity with SEQ ID NO: 1, or a degree of sequence identity falling within a range between any of the foregoing) and including SEQ ID No. 2 (or a polynucleotide operative for expression of components for the secretion of Enterocin A including at least about 70, 80, 85, 90, 92, 95, 98, 99 or 100% sequence identity with SEQ ID NO: 2, or a degree of sequence identity falling within a range between any of the foregoing).

Embodiments herein can specifically include the intestinal tract bacterium *E. coli* strain GP00700 deposited under ATCC Accession No. PTA-126596, the bacterium further comprising an exogenous polynucleotide including SEQ ID No. 1 (or a polynucleotide operative for expressing Enterocin A including at least 70, 80, 85, 90, 92, 95, 98, 99 or 100% sequence identity with SEQ ID NO: 1, or a degree of sequence identity falling within a range between any of the foregoing) and SEQ ID No. 2 (or a polynucleotide operative for expression of components for the secretion of Enterocin A including at least about 70, 80, 85, 90, 92, 95, 98, 99 or 100% sequence identity with SEQ ID NO: 2, or a degree of sequence identity falling within a range between any of the foregoing).

Embodiments herein can include a polynucleotide including SEQ ID No. 1 (or a polynucleotide operative for expressing Enterocin A including at least about 70, 80, 85, 90, 92, 95, 98, 99 or 100% sequence identity with SEQ ID NO: 1, or a degree of sequence identity falling within a range between any of the foregoing) and including SEQ ID No. 2 (or a polynucleotide operative for expression of components for the secretion of Enterocin A including at least about 70, 80, 85, 90, 92, 95, 98, 99 or 100% sequence identity with SEQ ID NO: 2, or a degree of sequence identity falling within a range between any of the foregoing).

In some embodiments, a method for preventing, alleviating or treating necrotic enteritis in an animal caused by *Clostridia perfringens* is included herein. The method can include a step of identifying an animal in need thereof. The method can include a step of administering an effective amount of a composition (such as any of the aforementioned compositions) to an animal in need thereof. In some embodiments, the animal is a mammal. In some embodiments, the mammal is a human, a dog, a cat, or a pig. In some embodiments, the animal is a bird. In some embodiments, the bird is chicken, a turkey or a duck. In some embodiments, the animal is a fish.

In some embodiments, a method for restoring rate of weight gain in an animal that has necrotic enteritis caused by *C. perf.* is included herein. In some embodiments, the method can include a step of administering to an animal in need thereof an effective amount of a composition such as any of the aforementioned compositions. In some embodiments, the animal is a mammal. In some embodiments, the mammal is a pig. In some embodiments, the animal is a bird. In some embodiments, the bird is a chicken, a turkey or a duck.

It should be noted that, as used in this specification and the appended claims, the singular forms "a," "an," and "the" include plural referents unless the content clearly dictates otherwise. Thus, for example, reference to a composition containing "a bacterium" includes a composition with more than one bacterium. It should also be noted that the term "or" is generally employed in its sense including "and/or" unless the content clearly dictates otherwise.

It should also be noted that, as used in this specification and the appended claims, the word "engineered" describes a system, apparatus, or other structure that is constructed or configured to perform a particular task or adopt a particular configuration. The phrase "engineered" can be used interchangeably with other similar phrases such as arranged and configured, constructed and arranged, constructed, manufactured and arranged, and the like.

For any method disclosed herein that includes discrete steps, the steps may be conducted in any feasible order. And, as appropriate, any combination of two or more steps may be conducted simultaneously.

Embodiments described herein are not to be taken in isolation from the rest of the disclosure and, as such, can be combined with other features or embodiments as may be appropriate based on the general knowledge and understanding of a skilled reader.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects may be better understood with reference to the following examples. These examples are intended to be representative of specific embodiments but are not intended as limiting the overall scope of embodiments herein.

EXAMPLES

Herein, we describe the application of this invention for the delivery of the antimicrobial peptide Enterocin A to the intestines of animals.

Enterocin A is a bacteriostatic peptide with activity against *Clostridia* spp. Application of this invention results in low counts of *Clostridia perfringens* in the jejunum of chickens.

In embodiments herein, new *E. coli* strains are isolated from the intestinal tracts of healthy chickens. Embodiments herein include natural *E. coli* isolates GP00492-551, GP00666-811 (General Probiotics Inc. accession numbers 00492-00551 and 00666-00811).

In embodiments herein, isolated *E. coli* strains are characterized for virulence factors, antibiotic susceptibility and DNA fingerprints.

In embodiments herein, selected *E. coli* isolates are engineered for the expression and secretion of Enterocin A.

Enterocin A expression vectors are included for various *E. coli* probiotic species with the expression of all parts relying on recombinant expression systems.

Embodiments herein include genetically engineered *E. coli* isolates GP00492-551, and GP00666-811.

In embodiments herein, the DNA promoter used in a recombinant construct for the expression of Enterocin A is chosen from promoters presented in Table 5, including but not limited to the following group: constitutive (SEQ ID NOS: 3-5), FNRs (SEQ ID NO: 6), stationary phase (SEQ ID NO: 10), GadA/B (SEQ ID NOS: 7-8), and OsmB (SEQ ID NO: 9).

In embodiments herein, engineered *E. coli* are tested in assays that mimic the gastrointestinal tract environment. In embodiments herein, engineered *E. coli* are rank-ordered, screened and selected for animal experiments.

In embodiments herein, selected *E. coli* are administered to animals demonstrating the decrease of *C. perf.*-induced necrotic enteritis.

Example 1. *E. coli* Isolation from Intestinal Tracts of Chickens

In this example, we describe isolating a library of *E. coli* from the jejunum of healthy chickens and using these isolates as cellbot candidates.

Intestinal tracts of healthy chickens were excised from the birds and frozen at −20° C. prior to isolation. On the day of isolation, intestinal tracts were thawed at ~37° C. The small intestines were then spread out and separated into five approximately 12" long sections beginning at the proximal end of the duodenum. A wash bottle containing sterile water was then inserted in the proximal end of each segment and used to rinse the lumen contents out of each segment. Segments were then opened lengthwise using sterile surgical scissors and a sterile razor blade was used to separate the mucus layer from the intestinal wall. The mucus was then stored in a sterile 1.5 mL microcentrifuge tube.

To isolate *E. coli* from the mucus, 100 uL of mucus was directly plated on a 150 mm diameter MacConkey agar plate (Remel). Additional samples were also generated by adding 2 mL of lysogeny broth (Miller) to the remaining mucus (~500 uL to 1 mL of mucus) and allowed to incubate for 2 hours at 37° C. to assist in *E. coli* recovery.

The sample was then centrifuged at 3000 rcf for 2 minutes and 50 uL of the pellet was plated on another MacConkey agar plate. When necessary, 10 and 100× dilutions were performed prior to plating to obtain single colonies. The plates were incubated overnight (~20 hours) at 37° C. Colonies exhibiting lactose-fermenting *E. coli* morphology on MacConkey agar were saved for further evaluation.

To further verify that colonies on MacConkey plates were indeed *E. coli*, two independent colony Polymerase Chain Reaction (PCRs) were performed using primers that bind to the gadA and gadB promoter regions in the *E. coli* chromosome. PCRs were performed using GoTaq Green Mastermix with the parameters shown below. The primers, annealing temperatures, and expected band sizes are listed in Table 6.

*E. coli* Nissle 1917 as well as another verified *E. coli* isolate were used as positive controls. Detection of one or both PCRs with the expected band size signified positive *E. coli* identity. Five positive isolates from each segment from each bird were grown overnight in lysogeny broth and saved as freezer stocks at −80° C.

PCR Conditions: Initial Denaturation: 95° C. 2 minutes. Repeat 30×: 95° C. 1 minute, 45° C. 1 minute. 72° C. 30 seconds. Final extension: 5 minutes

TABLE 6

Primers used to verify *E. coli* identity

| Gene | Primers (Forward and Reverse, 5'-3') (Derived from *Escherichia coli*) | Annealing Temp-erature | Expected Amplicon Length (basepairs) |
|---|---|---|---|
| gadA | gadA F: GATCGCCCGAACAGCAATG (SEQ ID NO: 28)<br>gadA R: ATAAAAAAGTAGGATTTAT CCGC (SEQ ID NO: 29) | 45 | 174 |
| gadB | gadB F: TCAAGTACTAATAGTGATAT TTTAAGG (SEQ ID NO: 30)<br>gadB R: TTAAAAAAGTAGGATTTATC GATAAAG (SEQ ID NO: 31) | 45 | 242 |

Example 2. Virulence Marker Identification

In this example, we describe ensuring the isolated cellbot candidates do not contain certain virulence factors.

The following genes have been identified as being associated with Avian Pathogenic *E. coli* (APEC) virulence; cvaC, iroN, ompTp, hlyF, etsB, iss, aerJ/iutA, ireA, papC (Logue C M, et al. *Comparative analysis of phylogenetic assignment of human and avian ExPEC and fecal commensal Escherichia coli using the (previous and revised) clermont phylogenetic typing methods and its impact on avian pathogenic Escherichia coli (APEC) classification. Front. Microbiol.* 8, 2017).

Isolates were screened for the presence of these genes using colony PCR. PCRs were run for each gene using the primers listed in Table 7. Primer sequences were obtained from Logue et al. 2017. PCRs were performed using GoTaq Green Mastermix with the parameters shown below. Control strains known to contain or lack each gene of interest were included in all PCRs. Strains exhibiting PCR products at the expected DNA length were considered positive for a virulence gene. In general, strains exhibiting none of the above virulence factors were preferentially selected. Note that the presence of a virulence gene does not necessarily indicate pathogenicity of a strain. However, the genes are enriched in APEC strains compared to non-pathogenic E. coli (Johnson T J, et al. *Identification of minimal predictors of avian pathogenic Escherichia coli virulence for use as a rapid diagnostic tool. J. Clin. Microbiol.* 2008, 46, 3987-3996).

PCR Conditions: Initial Denaturation: 95° C. 2 minutes. Repeat 30x: 95° C. 1 minute, See Annealing Temperatures in Table 7, 1 minute, 72° C. 1 minute. Final extension: 5 minutes.

genome of a species. When a PCR is performed on a strain using these primers, it generates a unique set of product bands which can be used to differentiate between strains (Dombek P E, et al. *Use of repetitive DNA sequences and the PCR to differentiate Escherichia coli isolates from human and animal sources. Appl. Environ. Microbiol.* 2000, 66, 2572-2577). The BOX AIR primer was used differentiate among E. coli isolates. PCRs were performed using GoTaq Green Master Mix (Promega) with the following PCR

TABLE 7

Primers used for virulence factor screening

| Gene | Primers (Forward and Reverse, 5'-3') (Derived from Escherichia coli) | Annealing Temperature ° C. | Expected Amplicon Length (basepairs) |
|---|---|---|---|
| cvaC | cvaC_F CACACACAAACGGGAGCTGTT (SEQ ID NO: 32)<br>cvaC_R CTTCCCGCAGCATAGTTCCAT (SEQ ID NO: 33) | 55 | 676 |
| iroN | iroN_F AAGTCAAAGCAGGGGTTGCCCG (SEQ ID NO: 34)<br>iroN_R GACGCCGACATTAAGACGCAG (SEQ ID NO: 35) | 57 | 667 |
| ompTp | ompTp_F TCATCCCGGAAGCCTCCCTCACTACTAT (SEQ ID NO: 36)<br>ompTp_R TAGCGTTTGCTGCACTGGCTTCTGATAC (SEQ ID NO: 37) | 61 | 495 |
| hlyF | hlyF_F GGCGATTTAGGCATTCCGATACTC (SEQ ID NO: 38)<br>hlyF_R ACGGGGTCGCTAGTTAAGGA (SEQ ID NO: 39) | 56 | 598 |
| etsB | etsB_F CAGCAGCGCTTCGGACAAAATCTCCT (SEQ ID NO: 40)<br>etsB_R TTCCCCACCACTCTCCGTTCTCAAAC (SEQ ID NO: 41) | 61 | 379 |
| Iss | Iss_F CAGCAACCCGAACCACTTGATG (SEQ ID NO: 42)<br>Iss_R AGCATTGCCAGAGCGGCAGAA (SEQ ID NO: 43) | 57 | 324 |
| aerJ/iutA | aerJ/iutA_F GGCTGGACATCATGGGAACTGG (SEQ ID NO: 44)<br>aerJ/iutA_R CGTCGGGAACGGGTAGAATCG (SEQ ID NO: 45) | 58 | 301 |
| ireA | ireA_F GATGACTCAGCCACGGGTAA (SEQ ID NO: 46)<br>ireA_R CCAGGACTCACCTCACGAAT (SEQ ID NO: 47) | 54 | 259 |
| papC | papC_F GTGGCAGTATGAGTAATGACCGTTA (SEQ ID NO: 48)<br>papC_R ATATCCTTTCTGCAGGGATGCAATA (SEQ ID NO: 49) | 53 | 202 |

Example 3. Antibiotic Resistance Screening

In this example, we describe characterizing the susceptibility of cellbot candidates to various classes of antibiotics.

Antibiotic resistance was tested for the following antibiotics: rifampicin (100 ug/mL), nalidixic acid (20 ug/mL), chloramphenicol (20 ug/mL), ampicillin (100 ug/mL), kanamycin (50 ug/mL), and spectinomycin (100 ug/mL). E. coli isolates were struck out on lysogeny broth (LB) agar and grown overnight at 37° C. The following day, E. coli from the LB plates was struck on LB agar growth plates containing the above concentrations of antibiotic. The plates were incubated overnight at 37° C. Growth was recorded as positive, negative, or minor depending on the density of the resulting E. coli patch. Isolates exhibiting no antibiotic resistance were preferentially used for further study.

Example 4. E. coli Isolate Fingerprinting

In this example, we describe fingerprinting the library of E. coli isolates.

DNA fingerprinting was used to characterize isolates and to ensure that isolates were in fact unique from one another. This is particularly important when isolating different strains within the same bird. DNA fingerprinting uses a single primer that binds randomly but reproducibly throughout the conditions: Initial Denaturation: 95° C. 2 minutes. Repeat 30x: 95° C. 1 minute, 50° C. 1 minute, 72° C. 8 minutes. Final extension: 8 minutes.

Example 5. Serotyping of E. coli Isolates

All isolated E. coli were tested for the following serotypes: O26, O55, O103, O111, O121, O128abc, O145, O157, O45. These serotypes include "the Big Six" E. coli serotypes that are monitored in the US meat industry. These serotypes, along with O157, are the most common E. coli serotypes found in food. They produce Shiga toxins that can result in severe intestinal infections in humans.

The O45 single antiseria (product number 85042) and the O Pool 1 EPEC & VTEC/STEC (product number 48229) tests from Statens Serum Institut (SSI) were used to test for the aforementioned serotypes.

Probiotics were grown overnight in Brain Heart Infusion (BHI) medium. The following day, the cultures were autoclaved (along with a negative BHI control lacking cells) at 121° C. for two hours to remove possible K capsules and cross reactivity. Cultures were then allowed to settle for 1 hour at room temperature. 80 uL of the antiserum was then combined with 80 uL of autoclaved cultures and controls in a sterile round-bottom 96 well plate. The plate was then sealed in a Ziplock bag and incubated overnight at 50° C.

Cultures exhibiting agglutination were deemed positive for the serotypes. Positive controls were included (ex. *E. coli* 0157 H7 EDL #933 was used for the O Pool 1) and were found to agglutinate. Additionally, auto agglutinating was tested by using phosphate buffered saline (PBS) rather than O antiserum. Cultures that exhibited agglutination in PBS were not able to be tested for serotype and were eliminated as candidates.

Example 6. Assembly of a Set of DNA Sequences for the Expression and Secretion of Enterocin A To generate the modified GP strains, *E. coli* was transformed with plasmid pKG00255. The engineered strain expresses Enterocin A and employs the Microcin V secretion genes (cvaA and cvaB) to secrete the peptide. This genetic construct contains promoters from the Anderson promoter collection (J23100-J23119) as well as promoters derived from then native *E. coli* microcin V genetic cluster. Specifically, J23100 was used as promoter controlling the expression of Enterocin A, and native secretion system promoter as promoter controlling the expression of Microcin V secretion genes. These components are incorporated in a high copy number plasmid containing the pMB1 origin of replication for *E. coli.*

Figure 2:
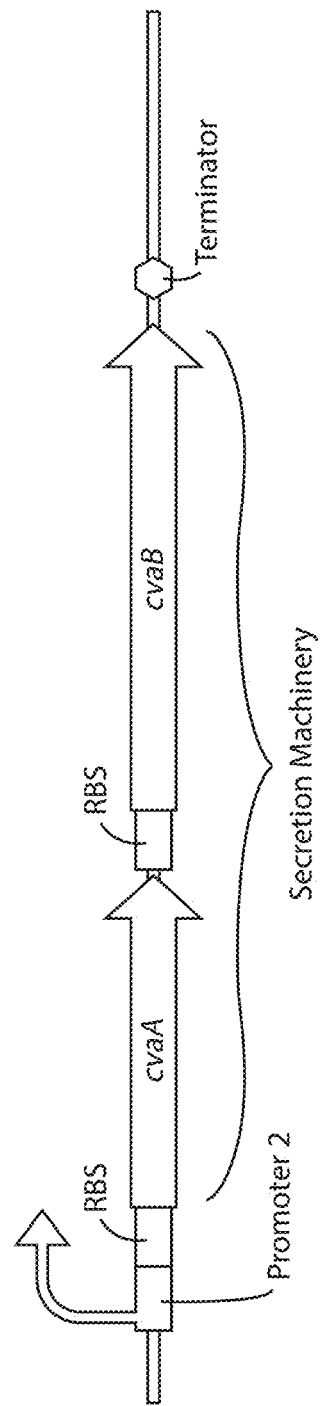
Figure 3:
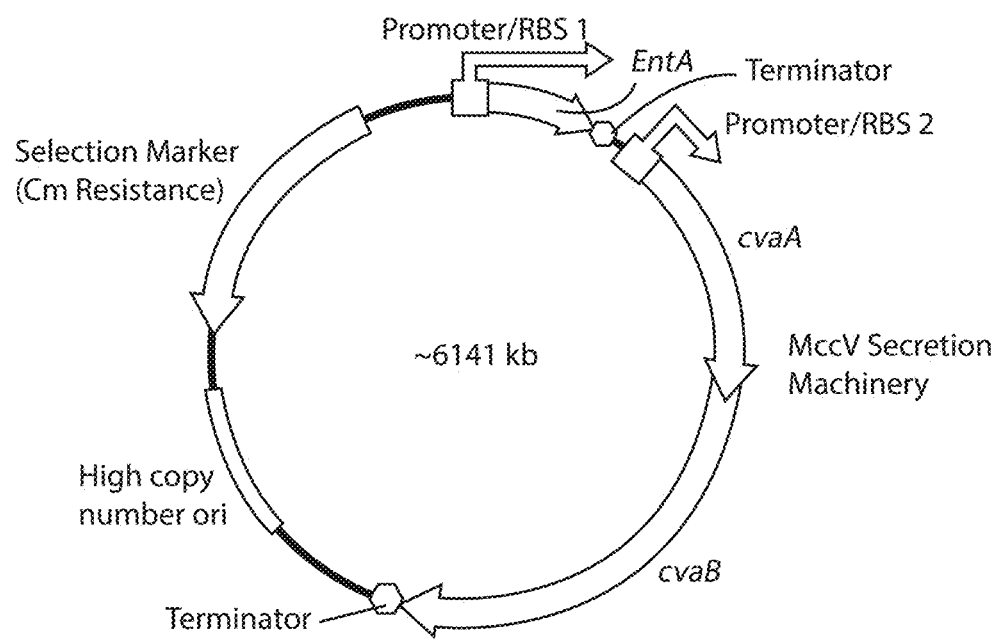

FIG. 1 is a schematic diagram of the engineered Enterocin transcriptional unit including an assembled DNA sequence of a promoter, a ribosome binding site, enterocin A, and a transcription terminator site. FIG. 2 is a schematic diagram of the secretion system transcriptional unit, including the genes cvaA and cvaB of the Microcin V secretion systems, the diagram specifically illustrating an assembled DNA sequence of a promoter, a ribosome binding site for cvaA, cvaA, a ribosome binding site for cvaB, and a transcription terminator site. FIG. 3 is a schematic diagram of the plasmid map used to engineer cellbots for the expression of an antimicrobial peptide, the diagram specifically illustrating plasmid pKG00255 (SEQ ID No: 13) for the expression of an antimicrobial peptide (AMP) and the secretion machinery. The selection marker confers resistance to chloramphenicol.

Example 7. Transformation of DNA in Cellbot Variants

DNA constructs were first generated in standard cloning strains (ex. *E. coli* JM109 and *E. coli* MC1061 F'). Constructs were then isolated, sequence-verified, and transformed into the desired delivery host. *E. coli* isolated from poultry intestines were made electrocompetent using standard methods, including natural *E. coli* isolates GP00492-551 and GP00666-811.

Briefly, 100 mL of lysogeny broth (LB) was inoculated with 400 uL of an overnight culture of *E. coli* then incubated at 37C under agitation until the culture reaches an OD600 of ~0.4. The cells were pelleted down by centrifugation at 4000×g for 10 minutes and washed three times in ice cold deionized water. The final pellet was resuspended in 400 uL ice cold 10% glycerol in deionized water.

For transformation, 50 uL of electrocompetent cells were thawed on ice then mixed with 50-200 ng of vector. *E. coli* were transformed at 2400 V, 25 uF, 200 Ohms in a 0.2 um gap cuvette. The transformation was then incubated in 400 uL SOC medium for 1 hr at 37C and plated on LB agar containing the appropriate selective antibiotic.

Example 8. Stab-On-Agar Tests of Antimicrobial Activity of Cellbots Against *C. perf*

To test the activity of the modified cellbots, 50-150 uL *C. perf.* overnight culture was spread on Brain Heart Infusion (BHI) with agar plates to generate a lawn. A colony of the modified GP00837 was swabbed then stabbed into the agar and incubated anaerobically overnight at 37° C. FIG. 4 shows the result of this assay. The white dot at the center is the modified GP00837. The light background indicates *C. perf.* growth white the dark region is a zone of *C. perf.* growth-inhibition resulting from EntA secreted by GP00837. This example shows that engineered *E. coli* with pKG00255 shows high activity against strains of *C. perf.* in an agar diffusion assay in high nutrient agar.

Example 9. Supernatant Assays and Liquid Culture Assays of Antimicrobial Activity of Cellbots Against Indicator Strain To conduct these assays, colonies of the cellbots to be compared were inoculated in growth medium. Cultures are grown for 24 hours in an aerobic environment (shaking) at 37° C. After 24 hours, the cultures were centrifuged for one minute at 13,000×g to pellet the cells. The supernatant was then transferred to a new tube and sterilized by boiling at 100° C. for 10 minutes.

Peptide concentration of the supernatants was then compared by serially diluting each supernatant and testing the dilutions abilities to inhibit the indicator strain, or a strain known to be susceptible to the peptides. This essentially estimates a minimal inhibitory concentration (MIC) of each supernatant. The supernatant with the lowest MIC is the most potent.

In the experiment shown here, *Enterococcus faecium* 8E9 (EF) was used as the indicator strain rather than *C. perf.* because of its robust growth. This enabled more reliable quantitative comparisons across producer strains. These results were shown to be translatable to *C. perf.* by demonstrating a linear correlation between EF and *C. perf.* susceptibility to the cellbots in question.

To determine the MIC, the indicator strain was grown overnight in rich medium. The following day, the indicator strain was diluted in rich medium to give ~10E3-10E4 CFU/mL. 30 uL of the probiotic supernatants were loaded into the first two rows of a sterile 96 well plate. 30 uL of phosphate buffered saline (PBS) was loaded into the remaining rows. 2× serial dilutions are performed from row 2 to row 8. 270 uL of the diluted indicator strain culture was then added to each well. This gives a series of 8 2× dilutions of supernatant giving concentrations from 10% v/v to 0.08% v/v.

The indicator plate was covered and incubated statically for 24 hours at 37° C. The following day, the last dilution exhibiting no growth was recorded for each supernatant tested. These data were then used to compare potency of each supernatant.

TABLE 8 shows the activities of twelve different probiotic organisms containing three different constructs (total of 36 probiotic strains) grown in rich growth medium (lysogeny broth). Cellbot activities are shown as the reciprocal of the lowest volumetric fraction of supernatant capable of inhibiting the indicator strain. For example, 1% v/v supernatant from probiotic GP00835 with the high constitutive promoter was sufficient to inhibit pathogen growth. The reciprocal is taken only to make the data more intuitive so that a higher value indicates a higher activity level.

TABLE 8

Supernatant minimum inhibitory activities to compare Enterocin production

| GP Strain | Species | Strain | Promoter | Inhibitory Fraction | Activity |
|---|---|---|---|---|---|
| 00632 | E. coli | Chicken Ceca Isolate | anaerobic | 0.04 | 28 |
| 00639 | E. coli | Human Isolate | anaerobic | 0.04 | 28 |
| 00816 | E. coli | Chicken SI 1 | anaerobic | 0.10 | 10 |
| 00817 | E. coli | Chicken SI 2 | anaerobic | 0.17 | 6 |
| 00818 | E. coli | Chicken SI 3 | anaerobic | 0.20 | 5 |
| 00819 | E. coli | Chicken SI 4 | anaerobic | 0.17 | 6 |
| 00820 | E. coli | Chicken SI 5 | anaerobic | 0.05 | 20 |
| 00821 | E. coli | Chicken SI 6 | anaerobic | 0.04 | 24 |
| 00822 | E. coli | Chicken SI 7 | anaerobic | 0.20 | 5 |
| 00823 | E. coli | Chicken SI 8 | anaerobic | 0.05 | 20 |
| 00824 | E. coli | Chicken SI 9 | anaerobic | 0.03 | 34 |
| 00825 | E. coli | Chicken SI 10 | anaerobic | 0.10 | 10 |
| 00635 | E. coli | Chicken Ceca Isolate | high constitutive | 0.05 | 20 |
| 00638 | E. coli | Human Isolate | high constitutive | 0.05 | 20 |
| 00833 | E. coli | Chicken SI 1 | high constitutive | 0.02 | 48 |
| 00834 | E. coli | Chicken SI 2 | high constitutive | 0.05 | 20 |
| 00835 | E. coli | Chicken SI 3 | high constitutive | 0.01 | 95 |
| 00836 | E. coli | Chicken SI 4 | high constitutive | 0.20 | 5 |
| 00837 | E. coli | Chicken SI 5 | high constitutive | 0.03 | 34 |
| 00838 | E. coli | Chicken SI 6 | high constitutive | 0.03 | 40 |
| 00839 | E. coli | Chicken SI 7 | high constitutive | 0.08 | 12 |
| 00840 | E. coli | Chicken SI 8 | high constitutive | 0.03 | 34 |
| 00841 | E. coli | Chicken SI 9 | high constitutive | 0.04 | 24 |
| 00842 | E. coli | Chicken SI 10 | high constitutive | 0.05 | 20 |
| 00633 | E. coli | Chicken Ceca Isolate | medium constitutive | 0.10 | 10 |
| 00636 | E. coli | Human Isolate | medium constitutive | 0.04 | 28 |
| 00843 | E. coli | Chicken SI 1 | medium constitutive | 0.05 | 20 |
| 00844 | E. coli | Chicken SI 2 | medium constitutive | 0.20 | 5 |
| 00845 | E. coli | Chicken SI 3 | medium constitutive | 0.08 | 12 |
| 00846 | E. coli | Chicken SI 4 | medium constitutive | 0.20 | 5 |
| 00847 | E. coli | Chicken SI 5 | medium constitutive | 0.20 | 5 |
| 00848 | E. coli | Chicken SI 6 | medium constitutive | 0.10 | 10 |
| 00849 | E. coli | Chicken SI 7 | medium constitutive | 0.20 | 5 |
| 00850 | E. coli | Chicken SI 8 | medium constitutive | 0.20 | 5 |
| 00851 | E. coli | Chicken SI 9 | medium constitutive | 0.10 | 10 |
| 00852 | E. coli | Chicken SI 10 | medium constitutive | 0.05 | 20 |

FIG. 5 shows a graph of C. perf. growth in nutrient rich media (thioglycolate with 2% beef extract) over time comparing the effects of supernatant from a probiotic producing Enterocin A, Enterocin B, and Hiracin JM79 under high-nutrient conditions versus no treatment. This example shows that the peptides secreted by the probiotic engineered with a high nutrient promoter suppresses C. perf. growth in nutrient rich media.

A supernatant colony-counting assay was used to obtain these data. For this assay 10 uL of an overnight culture of C. perf. was inoculated into 900 uL Thioglycollate+2% beef extract. 100 uL of supernatant from either a probiotic producing no peptides (Control) or the same strain producing the three peptides Enterocin A, Enterocin B, and Hiracin JM79 (BHA) was then added to the culture. The culture was then incubated at 37° C. under anaerobic conditions.

10 uL samples of each culture was taken at 0 hours, 3 hours, 6 hours, and 24 hours and serially diluted in a series of 6 10× dilutions. Dilutions were plated on selective agar (Brain heart infusion with 100 ug/mL rifampicin and 30 ug/mL nalidixic acid). Plates were incubated overnight under anaerobic conditions at 37° C. and colonies of *C. perf.* were counted. Based on the number of colonies, the colony forming units (CFU) of *C. perf.* per mL of culture were determined for each time point.

Example 10. Testing and Screening of Cellbots in Stomach-Like Environments

In order to be delivered to the site of infection intact, it is beneficial that the cellbots survive passage through the acidic conditions of the stomach. Cellbots were thus tested for their sensitivity to stomach contents using survival assays in vitro. For these assays, contents were removed from the gizzards of healthy chickens and were mixed with water (~1:1 ratio). The mixture was then centrifuged for 1 minute at 3500 rcf to remove large solids. The pH was measured for each experiment (pH ~2). Gizzard contents were then inoculated with ~107 CFU/mL of each probiotic. The cultures were then incubated anaerobically at 37° C. for 45 minutes. This time was selected as a conservative estimate of the residence time in the chicken gizzard.

The probiotic was enumerated at 0 hours and at 45 minutes by dilution plating on selective agar (BHI or LB+150 ug/mL rifampicin). Plates were incubated overnight at 37° C. and the CFU/mL were determined for both time points. The survival ratio of each strain was then calculated as follows:

Survival Ratio=(CFU/mL after incubation)/(CFU/mL before incubation) Table 9 shows the survival ratios of 30 different probiotics tested. Probiotics exhibiting particularly low survival ratios (ex. <0.2) were retested.

TABLE 9

Survival of probiotics in chicken gizzard contents

| GP Strain | Pre incubation CFU/mL | Post-incubation CFU/mL | RATIO |
|---|---|---|---|
| 00632 | 1.60E+07 | 3.20E+07 | 2.0 |
| 00635 | 3.60E+07 | 6.00E+07 | 1.7 |
| 00638 | 2.30E+07 | 4.10E+07 | 1.8 |
| 00639 | 1.40E+07 | 2.90E+07 | 2.1 |
| 00636 | 2.60E+07 | 3.00E+07 | 1.2 |
| 00816 | 3.00E+07 | 5.10E+07 | 1.7 |
| 00818 | 1.50E+07 | 3.00E+07 | 2.0 |
| 00823 | 5.30E+04 | 2.40E+05 | 4.5 |
| 00824 | 1.10E+07 | 3.00E+07 | 2.7 |
| 00825 | 1.40E+07 | 5.10E+06 | 0.4 |
| 00833 | 1.20E+07 | 1.20E+07 | 1.0 |
| 00834 | 3.10E+06 | 4.40E+06 | 1.4 |
| 00835 | 3.90E+06 | 4.30E+06 | 1.1 |
| 00836 | 1.40E+07 | 7.00E+06 | 0.5 |
| 00837 | 1.10E+07 | 7.10E+06 | 0.6 |
| 00838 | 1.50E+04 | 1.10E+05 | 7.3 |
| 00839 | 2.20E+06 | 3.80E+06 | 1.7 |
| 00840 | 1.40E+04 | 1.00E+05 | 7.1 |
| 00841 | 4.00E+07 | 3.10E+07 | 0.8 |
| 00842 | 1.50E+06 | 6.30E+05 | 0.4 |
| 00843 | 2.80E+07 | 2.40E+07 | 0.9 |
| 00844 | 5.30E+06 | 4.00E+06 | 0.8 |
| 00845 | 1.70E+07 | 1.20E+07 | 0.7 |
| 00846 | 1.20E+07 | 1.60E+07 | 1.3 |
| 00847 | 2.20E+07 | 1.40E+07 | 0.6 |
| 00848 | 5.60E+04 | 3.60E+04 | 0.6 |

TABLE 9-continued Survival of probiotics in chicken gizzard contents

| GP Strain | Pre incubation CFU/mL | Post-incubation CFU/mL | RATIO |
|---|---|---|---|
| 00849 | 4.30E+06 | 2.90E+06 | 0.7 |
| 00850 | 6.60E+04 | 4.50E+05 | 6.8 |
| 00851 | 4.10E+07 | 2.20E+07 | 0.5 |
| 00852 | 5.30E+06 | 4.20E+06 | 0.8 |

In addition to testing survival in stomach contents, survival was also tested in M9 minimal medium that had been adjusted to a pH of 2. This was done to test the impact of pH on the cells in the absence of any other variable biological components. Table 10 shows the survival ratios of 11 different isolates in stomach contents and M9 with HCl after 24 hours of incubation. Note that despite the same pH of ~2 in both media, isolates appear more sensitive in M9 adjusted with HCl.

TABLE 10

Survival ratios of probiotics after 24 hours in stomach contents or M9 (pH = 2)

| GP Strain | Stomach | M9 + HCl |
|---|---|---|
| 00801 | 1.13E+00 | 1.55E−01 |
| 00802 | 1.30E−01 | 1.60E−01 |
| 00803 | 3.23E−01 | 1.50E−01 |
| 00804 | 6.86E−01 | 5.71E−03 |
| 00805 | 7.74E−01 | 3.60E−03 |
| 00806 | 8.00E−01 | 1.88E−04 |
| 00807 | 1.07E+00 | 0.00E+00 |
| 00808 | 5.67E−01 | 0.00E+00 |
| 00809 | 8.71E−01 | 0.00E+00 |
| 00810 | 9.00E−01 | 0.00E+00 |
| 00811 | 6.32E−01 | 2.08E−01 |

Example 11. Testing and Screening of Cellbots in Bile Acid Contents

In order to be delivered to the site of infection intact, it is beneficial that the cellbots also survive passage through the bile of the duodenum. Cellbots were thus tested for their sensitivity to chicken bile using survival assays in vitro. For these assays, contents were removed from the duodenums of healthy chickens centrifuged for 1 minute at 3500 rcf to remove large solids. Duodenum contents were then inoculated with ~107 CFU/mL of each probiotic. The cultures were then incubated anaerobically at 37° C. for 2 hours. This time was selected as a conservative estimate of the residence time in the chicken duodenum.

The probiotic was enumerated at 0 hours and at 2 hours by dilution plating on selective agar (BHI or LB+150 ug/mL rifampicin). Plates were incubated overnight at 37° C. and the CFU/mL were determined for both time points. The survival ratio of each strain was then calculated as follows:

Survival Ratio=(*CFU/mL* after incubation)/(*CFU/mL* before incubation)

Table 11 shows the survival ratios of 30 different probiotics tested. Probiotics exhibiting particularly low survival ratios (ex. <0.2, shown in grey) were retested.

TABLE 11

Survival of probiotics in chicken bile

| GP Strain | Pre incubation CFU/mL | Post-incubation CFU/mL | RATIO |
|---|---|---|---|
| 00632 | 4.00E+07 | 2.00E+07 | 0.5 |
| 00635 | 8.00E+07 | 4.40E+07 | 0.6 |
| 00638 | 5.10E+07 | 3.90E+07 | 0.8 |
| 00639 | 5.40E+07 | 2.90E+07 | 0.5 |
| 00636 | 5.40E+07 | 3.00E+07 | 0.6 |
| 00816 | 4.10E+07 | 5.20E+07 | 1.3 |
| 00818 | 2.80E+07 | 3.30E+07 | 1.2 |
| 00823 | 5.10E+05 | 4.50E+06 | 8.8 |
| 00824 | 2.30E+07 | 1.60E+07 | 0.7 |
| 00825 | 3.00E+07 | 5.10E+06 | 0.2 |
| 00833 | 4.90E+07 | 2.90E+07 | 0.6 |
| 00834 | 1.00E+07 | 1.10E+07 | 1.1 |
| 00835 | 2.20E+07 | 1.30E+07 | 0.6 |
| 00836 | 2.80E+07 | 3.20E+06 | 0.1 |
| 00837 | 3.20E+07 | 3.60E+07 | 1.1 |
| 00838 | 1.70E+05 | 2.60E+06 | 15.3 |
| 00839 | 2.40E+06 | 1.40E+07 | 5.8 |
| 00840 | 7.30E+04 | 1.90E+06 | 26.0 |
| 00841 | 5.50E+07 | 5.60E+07 | 1.0 |
| 00842 | 2.70E+06 | 1.70E+06 | 0.6 |
| 00843 | 5.40E+07 | 4.10E+07 | 0.8 |
| 00844 | 5.50E+06 | 4.60E+06 | 0.8 |
| 00845 | 3.90E+07 | 3.40E+07 | 0.9 |
| 00846 | 4.80E+07 | 1.70E+07 | 0.4 |
| 00847 | 3.20E+07 | 2.40E+07 | 0.8 |
| 00848 | 4.60E+05 | 1.80E+06 | 3.9 |
| 00849 | 5.10E+06 | 4.10E+06 | 0.8 |
| 00850 | 5.40E+05 | 3.80E+06 | 7.0 |
| 00851 | 5.30E+07 | 2.50E+07 | 0.5 |
| 00852 | 1.00E+07 | 4.10E+06 | 0.4 |

Example 12. Growth and Stability of Cellbots in Jejunum-Like Environments

For the cellbots to be effective, they are preferably metabolically active inside the poultry intestinal tracts act the site of infection. In NE, the *C. perf* proliferation largely occurs in the mucosal layer of the small intestinal tract. Thus, it is desirable to select a delivery strain that can proliferate in the SI mucus layer, indicating metabolic activity. To test this parameter, SI mucus from the jejunum and ileum were isolated. The mucus was then diluted 10× in M9 minimal medium and sterile filtered to generate the biomatrix growth medium. A similar assay can be done using mucus isolated from the ceca.

To perform the assay, the probiotic was first grown overnight in lysogeny broth (LB). 2.5 uL of the overnight culture was then added to 250 uL of the biomatrix growth medium in a sterile 96 well plate. The plate was then incubated at 37° C. with agitation in a plate reader. Growth was monitored continuously for 20 hours based on optical density at 600 nm.

FIG. 6 shows the growth curves of four different intestinal isolates in rich medium (LB) as well as 10× diluted SI mucus. Note that GP00105 exhibits poor growth compared to the other three strains in SI mucus but not in rich medium. This suggests that this particular strain may exhibit suboptimal metabolic activity inside the gut of animals.

Example 13. Antimicrobial Activity in Biomatrix Assays

*C. perf.* is largely believed to proliferate in the mucosal layer in the small intestines of chickens. It is thus desirable that the probiotics be active against *C. perf.* under the conditions found in this mucus layer. Supernatant activity assays, similar to those in Example 8, were used to verify that the peptides are active in the nutrients available at the site of infection.

For these assays, intestines were isolated from healthy chickens that were sacrificed at a poultry research facility. The intestines were then divided into their primary components—the duodenum, the ileum, the jejunum, and the ceca. Each section was then rinsed with sterile deionized water to remove the lumen contents. The sections were then cut lengthwise using a sterile razor blade and the mucus layer was gently scraped and saved in a sterile vial.

FIG. 7 shows the supernatant inhibition assay performed in dilute small intestinal and ceca mucus. For this assay, mucus was harvested from the ileum and jejunum (for small intestinal) or the ceca of healthy chickens as described above. The mucus was diluted 1:10 with M9 minimal medium then filter-sterilized. 10 uL of an overnight culture of *C. perf.* was inoculated into 900 uL of the diluted mucus. 100 uL of supernatant from either a probiotic producing no peptides (Control) or the same strain producing the three peptides Enterocin A, Enterocin B, and Hiracin JM79 (BHA) was then added to the culture. The culture was then incubated at 37° C. under anaerobic conditions.

10 uL samples of each culture was taken at 0 hours, 3 hours, 6 hours, and 24 hours and serially diluted in a series of 6 10× dilutions. Dilutions were plated on selective agar (Brain heart infusion with 100 ug/mL rifampicin and 30 ug/mL nalidixic acid). Plates were incubated overnight under anaerobic conditions at 37° C. and colonies of *C. perf.* were counted. Based on the number of colonies, the colony forming units (CFU) of *C. perf.* per mL of culture were determined for each time point.

Based on the results from the figures, it appears the peptides are active in the nutrients available in both the small intestine and ceca mucosal layers but to different extents.

Example 14. Rank-Ordering and Screening of Cellbots

For each of the screening experiments described in previous Examples, a scheme was employed to rank-order the *E. coli* isolates. For example, in Example 12 a procedure is described for assessing the growth of isolates in environments mimicking the jejunum mucus of chickens. The OD600 measurement is recorded at various time points and the isolates are ranked accordingly. In Table 12, 10 strains are ranked based on the OD600 measurement at 40 hours.

TABLE 12

Example rank-ordering of isolates according to their growth in chicken jejunum mucus environments (Example 12).

| Number | Strain | OD600 40 hr | Rank |
|---|---|---|---|
| 1 | GP000694 | 0.24 | 3 |
| 2 | GP000695 | 0.1 | 7 |
| 3 | GP000696 | 0.11 | 6 |
| 4 | GP000699 | 0.21 | 5 |
| 5 | GP000700 | 0.25 | 2 |
| 6 | GP000701 | 0.08 | 9 |
| 7 | GP000706 | 0.26 | 1 |
| 8 | GP000809 | 0.05 | 10 |
| 9 | GP000810 | 0.1 | 8 |
| 10 | GP000811 | 0.24 | 4 |

In Table 13, *E. coli* engineered isolates are ranked according to the diameter of the halo measured in a stab-on-agar plate experiment, as described in Example 8.

TABLE 13

Example rank-ordering of cellbots according to their antimicrobial activity measured with the stab-on-agar test (Example 8)

| Number | Strain | Halo Diameter (mm) | Rank |
|---|---|---|---|
| 1 | GP000816 | 18 | 4 |
| 2 | GP000817 | 17 | 6 |
| 3 | GP000818 | 12.5 | 13 |
| 4 | GP000819 | 14 | 12 |
| 5 | GP000820 | 16.5 | 9 |
| 6 | GP000821 | 15.5 | 11 |
| 7 | GP000822 | 0 | 15 |
| 8 | GP000823 | 17 | 6 |
| 9 | GP000824 | 18 | 4 |
| 10 | GP000825 | 16 | 10 |

The rankings were compiled for 360 systems engineered and tested. A linear combination of ranking was calculated and a new global ranking order was determined.

The top five leading candidates, GP00824, GP00834, GP00632, GP00839, and GP00837 were renamed GPEC2019001 (or T5), GPEC2019002 (or T6), GPEC2019003 (or T7), GPEC2019004 (or T8), and GPEC2019005 (or T9). These five cellbots were prepared for proof of concept animal experiments, described in Example 14.

Example 14. Proof of Concept Animal Experiment

In this example, we describe animal experiments conducted for assessing the efficacy and safety of engineered *E. coli* isolates that have been tested and screened as described in Examples 1-13.

An animal experiment was conducted to test the efficacy and safety of five engineered probiotic *E. coli* on the control of gross lesion scores and mortality due to *C. perf.*-induced necrotic enteritis, when medicated through water from 0-21 days, in broilers raised in battery cages for 22 days.

This study utilized 540 single-sex commercial broilers from a commercial hatchery. Each cage was considered an experimental unit. The study began on Study Day 0 (arrival of birds). There were nine (n=9) treatment groups (two negative controls, one positive control, five test article groups with challenge and one test article group without challenge) as shown in Table 14.

Each treatment group had 6 replicates. Each replicate contained 10 birds. There were 60 birds per treatment group. Treatment groups were represented as T1, T2, T3, T4, T5, T6, T7 T8 and T9.

On study day 0, eleven apparently healthy chicks were enrolled into each cage. On study day 7, each cage was corrected to have exactly 10 chicks per cage.

Except T1 and T3 treatment groups, all other treatment groups were medicated with their respective test article from very first (Day 0) drinking water until the last day of the study (Day 21).

Except T1 and T2 group, all other treatment groups were administered with mixture of *E. maxima* (10,000 sporulated oocyst/mL/bird)+*E. acervulina* (no limit) on day 14 through oral gavage.

Except T1 & T2 group, all other treatment groups were administered with *C. perf.* strain #16 at the rate of 2-9×10⁸ cfu/mL/bird on day 17 & 18 through oral gavage.

During the period of day 17-22, all the mortalities were necropsied.

TABLE 14

Description of groups in animal experiment (Example 14). Probiotic *E. coli* strains #1, #2, #3, #4, and #5 are GP00824, GP00834, GP00632, GP00839, and GP00837, respectively. "Best construct system alone" refers to GP00824, which had the highest global ranking.

| Treatment | Description | *C. perfringens* Challenge on Day 17 & 18 | Replicate Pens | Birds per Cage | Total No. Birds |
|---|---|---|---|---|---|
| T1 | Non-Challenged, Non-Treated Control | No | 6 | 10 | 60 |
| T2 | Best Construct System Alone (No Challenge) | No | 6 | 10 | 60 |
| T3 | Challenge Control | Yes | 6 | 10 | 60 |
| T4 | BMD Water Soluble During Day 18-21 | Yes | 6 | 10 | 60 |
| T5 | Probiotic *E. coli* Strain #1 | Yes | 6 | 10 | 60 |
| T6 | Probiotic *E. coli* Strain #2 | Yes | 6 | 10 | 60 |
| T7 | Probiotic *E. coli* Strain #3 | Yes | 6 | 10 | 60 |
| T8 | Probiotic *E. coli* Strain #4 | Yes | 6 | 10 | 60 |
| T9 | Probiotic *E. coli* Strain #5 | Yes | 6 | 10 | 60 |
| | | | Total Birds Used | | 540 |

The mortality results of the study are the following:
There were no mortalities observed in T1 & T2 groups.
The untreated challenge control group T3 had mortality of 32.8%.
Positive control T4 also had no mortality.
T5 construct system (GPEC2019001) showed highest mortality of 42.6%.
T6 (GPEC2019002) resulted in mortality of 14.8% (P<0.05).
T7 & T8 did not show statistically significant improvements in terms of mortality.
T9 (GPEC2019005) resulted in mortality of 11.3% (P<0.05).
T9 (GPEC2019005 or GP00837) is a cellbot with demonstrated performance in vivo, proving that a probiotic-based technology can have a profound effect on the mortality of broiler chickens caused by *C. perf.*-induced necrotic enteritis. Cellbot GP00837 (GPEC2019005) was formed using *E. coli* strain GP00700 deposited under ATCC Accession No. PTA-126596. This shows that GP00837 (GPEC2019005) is a highly useful *E. coli* strain for the creation of cellbots for treatment of animals and, in specific, chickens.

What was unexpected was that only two out of the five cellbots that ranked at the top of 360 engineered cellbots decreased necrotic enteritis induced mortality in chickens.

We did not observe any adverse effects on birds consuming probiotics, establishing the safety of the cellbots administered to chickens at the prescribed dosing regimen.

FIG. 8 is a graph demonstrating the lower mortality rate in birds challenged with *C. perf.* and necrotic enteritis treated with cellbot GP00837 (named GPEC2019005 in the animal study) compared to the mortality rate of untreated birds.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A composition for treatment of *C. perfringens* infection or *C. perfringens*-induced necrotic enteritis in an animal comprising
   a non-pathogenic *E. coli* bacterium isolated from an intestinal tract of an animal and transfected with a plasmid, the plasmid comprising a polynucleotide exogenous to the *E. coli* bacterium, the polynucleotide comprising
      a first heterologous promoter; and
      a first polynucleotide that encodes an antimicrobial protein, wherein the first polynucleotide is operably linked to the first heterologous promoter;
      a second heterologous promoter; and
      a second polynucleotide that encodes secretion genes, wherein the second polynucleotide is operably linked to the second heterologous promoter;
      wherein the plasmid has at least 95% sequence identity with SEQ ID NO: 13.

2. The composition of claim 1, wherein the *E. coli* bacterium is the *E. coli* strain GP00700 deposited under ATCC Accession No. PTA-126596 and the composition further comprises a pharmaceutically acceptable carrier.

3. The composition of claim 1, wherein the antimicrobial peptide has bacteriolytic or bacteriostatic activity against *Clostridium perfringens*.

4. The composition of claim 1, wherein the treated animal is a chicken.

5. The composition of claim 1, wherein the bacterium is isolated from a jejunum of healthy chickens.

6. The composition of claim 1, wherein the bacterium recolonizes a gastrointestinal tract of chicken infected with *Clostridium perfringens*.

7. The composition of claim 1, wherein the bacterium is metabolically active within a gastrointestinal tract of chicken.

8. The composition of claim 1, wherein the first heterologous promoter and the second heterologous promoter are selected to respond differently to exogenous environmental conditions found in a gastrointestinal tract of animals, the exogenous environmental conditions selected from the group consisting of nutrient content, oxygen content, pH and bile concentration.

9. The composition of claim 1, the plasmid comprising at least 98% sequence identity with SEQ ID NO: 13.

10. The composition of claim 1, the plasmid comprising 100% sequence identity with SEQ ID NO: 13.

11. A composition for treatment of *C. perfringens* infection or *C. perfringens*-induced necrotic enteritis in an animal comprising
   a non-pathogenic *E. coli* bacterium isolated from an intestinal tract of an animal comprising
      a polynucleotide exogenous to the *E. coli* bacterium comprising a polynucleotide sequence operative for expressing Enterocin A and with at least 95% sequence identity with SEQ ID No. 1; and a polynucleotide sequence operative for expressing components for the secretion of Enterocin A and with at least 95% sequence identity with SEQ ID No. 2.

12. The composition of claim 11, the *E. coli* bacterium comprising *E. coli* deposited under ATCC Accession No. PTA-126596.

13. The composition of claim 11, the exogenous polynucleotide comprising a polynucleotide sequence with 100% sequence identity with SEQ ID No. 1; and a polynucleotide sequence with 100% sequence identity with SEQ ID No. 2.

* * * * *

SEQUENCE LISTING

<160> NUMBER OF SEQ ID NOS: 50

<210> SEQ ID NO 1
<211> LENGTH: 424
<212> TYPE: DNA
<213> ORGANISM: Artificial Sequence
<220> FEATURE:
<223> OTHER INFORMATION: DNA sequence of construct to express Enterocin
      A

<400> SEQUENCE: 1
ttgacggcta gctcagtcct aggtacagtg ctagctactt acataacaac agcaacaact      60
aaggaggttt tcaatgcgca ctctgactct gaatgaatta gattctgttt ctggtggtac     120
cactcatagc ggtaagtatt acggaaatgg agtttactgt accaaaaata aatgcaccgt     180
tgattgggct aaagcgacaa cttgtatcgc tggtatgtct atcggcgggt tcttaggggg     240
tgccattcca ggcaaatgct aagcttggtc gaagctcaga ggatcgtaca ggcttccagg     300
catcaaataa aacgaaaggc tcagtcgaaa gactgggcct ttcgttttat ctgttgtttg     360

```
tcggtgaacg ctctctacta gagtcacact ggctcacctt cgggtgggcc tttctgcgtt    420
tata                                                                 424

<210> SEQ ID NO 2
<211> LENGTH: 3632
<212> TYPE: DNA
<213> ORGANISM: Escherichia coli

<400> SEQUENCE: 2
cctgataact ctcctatgtt gtatgtttat atgattttcc ttgaaacata taatgcaaat     60
tttcgattta ttttccatca ttaatccaga taaacaacaa actaatagta tgcaaggaga    120
cattatttgt ttcgccatga tgctttagaa aacagaaaaa tgaagtggca gggacgggca    180
atattacttc ccggaatacc actgtggtta atcatgctgg gaagcattgt gtttattacg    240
gcatttctga tgttcattat tgttggtacc tatagccgcc gtgttaatgt cagtggtgag    300
gtcacaacct ggccaagagc tgtcaatata tattcaggtg tacagggatt tgttgtcagg    360
cagtttgttc atgaagggca gttgataaaa aaggggatc ctgtttatct gattgacatc    420
agtaaaagta cacgcaatgg tattgtcact gataatcatc gccgggatat agaaaaccag    480
ctggttcgtg tggacaacat tatttcccgt ctggaagaaa gtaaaaaaat aacgctagat    540
accctggaaa acaacgtctg caatacaca gatgcgttcc gtcgctcatc agacattata    600
cagcgtgcag aggaagggat aaaaataatg aaaaataata tggagaatta cagatactat    660
cagtcaaaag gactgattaa taagatcaa ttaactaacc aagttgcatt atattatcaa    720
caacaaaaca accttctcag tctgagcgga caaaatgaac aaaatgccct gcagataacc    780
actctggaga gtcagattca gactcaggca gcagattttg ataatcgtat ctatcagatg    840
gaactgcaac gactcgaatt gcagaaagaa ctggttaaca ctgatgtgga aggcgaaatc    900
attatccggg cgttgtctga cgggaaagtt gactccctga gtgtcactgt agggcaaatg    960
gtcaataccg agacagcct tctgcaggtt attcctgaga acattgaaaa ctattatctt    1020
attctctggg tcccgaatga tgctgttcct tatatttcgg ctggtgacaa agtgaatatt    1080
cgttatgaag ccttcccctc agaaaaattt gggcagttct ctgctacggt taaaactata    1140
tccaggactc ctgcgtcaac acaggaaatg ttgacctata agggagcacc tcaaaatacg    1200
ccgggtgcct ctgttccctg gtataaagtc attgcgacgc ctgaaaagca gataatcagg    1260
tatgacgaaa atacctccc tctggaaaat ggaatgaaag ccgaaagtac actatttctg    1320
gaaaaaaggc gtatttacca gtggatgctt tctcctttct atgacatgaa acacagtgca    1380
acaggaccga tcaatgacta acaggaattt cagacaaatt ataaatctgc ttgatttgcg    1440
ctggcaacgt cgtgttccgg ttattcatca gacggagacc gctgaatgtg gactggcctg    1500
cctagcaatg atatgcggtc attttggtaa gaatattgac ctgatatatc ttcgccggaa    1560
gtttaatctc tctgcccgtg gagcaaccct tgcaggaata aatggaatag cggagcaact    1620
ggggatggcc acccgggctc tttcactgga gttggatgaa cttcgagtcc tcaaaacgcc    1680
gtgtattctc cactgggatt tcagtcactt cgtcgttctg gtcagcgtaa agcgtaaccg    1740
ttatgtactg catgatccgg ccaggggcat aagatatatc agccgggagg aaatgagccg    1800
atattttaca ggcgttgcac ttgaggtctg gcccggaagt gaattccagt cggaaaccct    1860
gcagacccgc ataagtcttc gttcactgat taacagtatt tacggtatta aagaacgct    1920 ggcgaaaatt ttctgtctgt cagttgtaat tgaagcaatc aatctgctaa tgccggtggg    1980
```

-continued

```
gacacagctg gttatggatc atgctattcc tgcggggac agagggctac tgacgctaat        2040
ttctgctgct cttatgtttt ttatattact caaagctgca acgagtacgc tgcgcgcatg        2100
gtcttcactg gttatgagca cgctcatcaa tgtacagtgg cagtcggggc tgttcgatca        2160
tcttctcaga ctaccgctgg cgttttttga acgccgaaaa ttaggtgata tccagtcacg        2220
ttttgactcc cttgacacat tgagggccac atttaccacc agtgtgatcg ggttcataat        2280
ggacagcatt atggttgtcg gtgtttgtgt gatgatgctg ttatacggag gatatctcac        2340
ctggatagtt ctctgcttta ccacaattta cattttatt cgactggtga catacggcaa        2400
ttaccgacag atatcagaag aatgtcttgt cagggaggcc cgtgccgcct cctattttat        2460
ggaaacatta tatggtattg ccacggtaaa aatccagggg atggtcggaa ttcgggggc        2520 acactggctt aatatgaaaa tagatgcgat aaattcgggt attaagctaa ccaggatgga        2580
tttgctcttc ggaggaataa ataccttttgt taccgcctgt gatcagattg taattttatg        2640
gctgggagca ggccttgtga tcgataatca gatgacaata ggaatgtttg tagcgtttag        2700
ttcttttcgt gggcagtttt cggaaagagt tgcctctctg accagttttc ttcttcagct        2760
aagaataatg agtctgcaca atgagcgcat tgcagatatt gcattacatg aaaaggagga        2820
aaagaaacct gaaattgaaa tcgttgctga tatgggccca atatccctgg aaaccaatgg        2880
tttaagctat cgttatgaca gtcagtcagc accgatattc agtgctctga gtttatctgt        2940
agctccgggg gaaagtgtgg ctataactgg tgcttccggt gcgggaaaaa ccacattaat        3000
gaaagtacta tgtggactat ttgaacctga tagcgggagg gtactgataa atggtataga        3060
tatacgccaa attggaataa ataattatca ccggatgata gcctgtgtta tgcaggatga        3120
ccggctattt tcaggctcaa ttcgtgaaaa tatctgtggt tttgcagagg aaatggatga        3180
agagtggatg gtagaatgtg ccagagcaag tcatattcat gatgttataa tgaatatgcc        3240
aatgggatat gaaacattaa taggtgaact tggggaaggt cttctggcg gtcaaaaaca        3300 gcgtatattt attgcacgag ccttataccg gaaaccagga atattattta tggatgaggc        3360
aaccagtgct cttgattcag agagtgaaca tttcgtgaat gttgccataa aaaacatgaa        3420
tatcaccagg gtaattattg cacacagaga aacaacgttg agaactgttg atagagttat        3480
ttctatttaa accatagagg aattacaagc gtatgaggaa tatttcttcc tgttataatt        3540
cctcgttatg ctcagatatc tgttggaggt ggaatggaag atagacaatc caccaagaag        3600
aaatatcatt ctgtgtggat tgtccaataa ct                                     3632

<210> SEQ ID NO 3
<211> LENGTH: 35
<212> TYPE: DNA
<213> ORGANISM: Artificial Sequence
<220> FEATURE:
<223> OTHER INFORMATION: DNA sequence of synthetic promoter J23109

<400> SEQUENCE: 3
tttacagcta gctcagtcct agggactgtg ctagc                                   35

<210> SEQ ID NO 4
<211> LENGTH: 35
<212> TYPE: DNA
<213> ORGANISM: Artificial Sequence
<220> FEATURE:
<223> OTHER INFORMATION: DNA sequence of synthetic promoter J23106

<400> SEQUENCE: 4
tttacggcta gctcagtcct aggtatagtg ctagc                                   35
```

<210> SEQ ID NO 5
<211> LENGTH: 35
<212> TYPE: DNA
<213> ORGANISM: Artificial Sequence
<220> FEATURE:
<223> OTHER INFORMATION: DNA sequence of synthetic promoter J23100

<400> SEQUENCE: 5
ttgacggcta gctcagtcct aggtacagtg ctagc                              35

<210> SEQ ID NO 6
<211> LENGTH: 150
<212> TYPE: DNA
<213> ORGANISM: Escherichia coli

<400> SEQUENCE: 6
agttgttctt attggtggtg ttgctttatg gttgcatcgt agtaaatggt tgtaacaaaa    60 gcaattttc cggctgtctg tatacaaaaa cgccgtaaag tttgagcgaa gtcaataaac    120
tctctaccca ttcagggcaa tatctctctt                                    150

<210> SEQ ID NO 7
<211> LENGTH: 174
<212> TYPE: DNA
<213> ORGANISM: Escherichia coli

<400> SEQUENCE: 7
gatcgcccga acagcaatgt tgggcgatt tttattacga taataaagtc tgttttaat     60 attatcatgt taaatgttta tattataaaa agtcgttttt ctgcttagga ttttgttatt   120
taaattaagc ctgtaatgcc ttgcttccat tgcggataaa tcctactttt ttat         174

<210> SEQ ID NO 8
<211> LENGTH: 242
<212> TYPE: DNA
<213> ORGANISM: Escherichia coli

<400> SEQUENCE: 8
tcaagtacta atagtgatat tttaaggtct gattttacg tgataattca ggagacacag    60
aatgcgcata aaataacag cataaaacac cttaccacca cccaagaatt tcatattgta    120 ttgttttca atgaaaaaat attattcgcg taatatctca cgataaataa cattaggatt   180
ttgttattta aacacgagtc ctttgcactt gcttacttta tcgataaatc ctacttttt    240 aa                                                                  242

<210> SEQ ID NO 9
<211> LENGTH: 63
<212> TYPE: DNA
<213> ORGANISM: Escherichia coli

<400> SEQUENCE: 9
ccctgcgcgc gagcagattt cacggaataa tttcaccaga cttattctta gctattatag   60
tta                                                                 63

<210> SEQ ID NO 10
<211> LENGTH: 260
<212> TYPE: DNA
<213> ORGANISM: Escherichia coli

<400> SEQUENCE: 10

```
tttttctta attgatggct aaatattctg aaataattag aaaaatgtat aaaaatccaa    60
aatattgtac taaatttgac cacttttgca gattgattag tttatggatg tttgtatcta   120
aatgatttta ttgataaatt actaaagcgt aatgattatt gatctcaatt gtattttgtg   180
ctaataaaat tctaacagaa ggacgtgagg ttcctctgta aaaatcatca tactatttcc   240
atcaaataag gaacgtaaaa                                                260
```

<210> SEQ ID NO 11
<211> LENGTH: 84
<212> TYPE: DNA
<213> ORGANISM: Artificial Sequence
<220> FEATURE:
<223> OTHER INFORMATION: DNA sequence of synthetic RBS of bicistronic
      design by Mutalik et al.

<400> SEQUENCE: 11

```
gggcccaagt tcacttaaaa aggagatcaa caatgaaagc aatttcgta ctgaaacatc    60 ttaatcatgc taaggaggtt ttct                                           84
```

<210> SEQ ID NO 12
<211> LENGTH: 129
<212> TYPE: DNA
<213> ORGANISM: Artificial Sequence
<220> FEATURE:
<223> OTHER INFORMATION: DNA sequence of synthetic transcriptional
      terminator

<400> SEQUENCE: 12

```
ccaggcatca aataaaacga aaggctcagt cgaaagactg ggcctttcgt tttatctgtt    60
gtttgtcggt gaacgctctc tactagagtc acactggctc accttcgggt gggcctttct   120
gcgtttata                                                            129
```

<210> SEQ ID NO 13
<211> LENGTH: 6141
<212> TYPE: DNA
<213> ORGANISM: Artificial Sequence
<220> FEATURE:
<223> OTHER INFORMATION: Full sequence of vector required for Enterocin
      A production and secretion from Escherichia coli

<400> SEQUENCE: 13

```
atcacgaggc agaatttcag ataaaaaaaa tccttagctt tcgctaagga tgatttctgg    60
aattcggtct ctggagttga cggctagctc agtcctaggt acagtgctag ctacttacat   120
aacaacagca acaactaagg aggttttcaa tgcgcactct gactctgaat gaattagatt   180
ctgtttctgg tggtaccact catagcggta agtattacgg aaatggagtt tactgtacca   240
aaaataaatg caccgttgat tgggctaaag cgacaacttg tatcgctggt atgtctatcg   300
gcgggttctt aggggtgcc attccaggca atgctaagc ttggtcgaag ctcagaggat   360
cgtacaggct tccaggcatc aaataaaacg aaaggctcag tcgaaagact gggcctttcg   420
ttttatctgt tgtttgtcgg tgaacgctct ctactagagt cacactggct caccttcggg   480
tgggcctttc tgcgtttata cgctcagagg agcctgataa ctctcctatg ttgtatgttt   540
atatgatttt ccttgaaaca tataatgcaa attttcgatt tattttccat cattaatcca   600
gataaacaac aaactaatag tatgcaagga gacattattt gtttcgccat gatgctttag   660
aaaacagaaa aatgaagtgg cagggacggg caatattact tcccggaata ccactgtggt   720
taatcatgct gggaagcatt gtgttttatta cggcatttct gatgttcatt attgttggta   780
```

```
cctatagccg ccgtgttaat gtcagtggtg aggtcacaac ctggccaaga gctgtcaata        840
tatattcagg tgtacaggga tttgttgtca ggcagtttgt tcatgaaggg cagttgataa        900
aaaaagggga tcctgtttat ctgattgaca tcagtaaaag tacacgcaat ggtattgtca        960
ctgataatca tcgccgggat atagaaaacc agctggttcg tgtggacaac attatttccc       1020
gtctggaaga aagtaaaaaa ataacgctag ataccctgga aaacaacgt ctgcaataca        1080
cagatgcgtt ccgtcgctca tcagacatta tacagcgtgc agaggaaggg ataaaaataa       1140
tgaaaataa tatggagaat tacagatact atcagtcaaa aggactgatt aataaagatc        1200
aattaactaa ccaagttgca ttatattatc aacaacaaaa caaccttctc agtctgagcg       1260
gacaaaatga acaaaatgcc ctgcagataa ccactctgga gagtcagatt cagactcagg       1320
cagcagattt tgataatcgt atctatcaga tggaactgca acgactcgaa ttgcagaaag       1380
aactggttaa cactgatgtg aaggcgaaa tcattatccg ggcgttgtct gacgggaaag        1440
ttgactccct gagtgtcact gtagggcaaa tggtcaatac cggagacagc cttctgcagg       1500
ttattcctga gaacattgaa aactattatc ttattctctg ggtcccgaat gatgctgttc       1560
cttatatttc ggctggtgac aaagtgaata ttcgttatga agccttcccc tcagaaaaat       1620
ttgggcagtt ctctgctacg gttaaaacta tatccaggac tcctgcgtca acacaggaaa       1680
tgttgaccta aagggagca cctcaaaata cgccgggtgc ctctgttccc tggtataaag        1740
tcattgcgac gcctgaaaag cagataatca ggtatgacga aaaatacctc cctctggaaa       1800
atggaatgaa agccgaaagt acactatttc tggaaaaaag gcgtatttac cagtggatgc       1860
tttctccttt ctatgacatg aaacacagtg caacaggacc gatcaatgac taacaggaat       1920
ttcagacaaa ttataaatct gcttgatttg cgctggcaac gtcgtgttcc ggttattcat       1980
cagacggaga ccgctgaatg tggactggcc tgcctagcaa tgatatgcgg tcatttggt       2040
aagaatattg acctgatata tcttcgccgg aagtttaatc tctctgcccg tggagcaacc       2100
cttgcaggaa tcaatggaat agcggagcaa ctggggatgg ccacccgggc tctttcactg       2160
gagttggatg aacttcgagt cctcaaaacg ccgtgtattc tccactggga tttcagtcac       2220
ttcgtcgttc tggtcagcgt aaagcgtaac cgttatgtac tgcatgatcc ggccaggggc       2280
ataagatata tcagccggga ggaaatgagc cgatatttta caggcgttgc acttgaggtc       2340
tggcccggaa gtgaattcca gtcggaaacc ctgcagaccc gcataagtct tcgttcactg       2400
attaacagta tttacggtat taaagaacg ctggcgaaaa ttttctgtct gtcagttgta       2460
attgaagcaa tcaatctgct aatgccggtg gggacacagc tggttatgga tcatgctatt       2520
cctgcgggg acagagggct actgacgcta atttctgctg ctcttatgtt ttttatatta       2580
ctcaaagctg caacgagtac gctgcgcgca tggtcttcac tggttatgag cacgctcatc       2640
aatgtacagt ggcagtcggg gctgttcgat catcttctca gactaccgct ggcgtttttt       2700
gaacgccgaa aattaggtga tatccagtca cgttttgact cccttgacac attgagggcc       2760
acatttacca ccagtgtgat cgggttcata atggacagca ttatggttgt cggtgtttgt       2820
gtgatgatgc tgttatacgg aggatatctc acctggatag ttctctgctt taccacaatt       2880
tacatttta ttcgactggt gacatacggc aattaccgac agatatcaga agaatgtctt       2940
gtcagggagg cccgtgccgc ctcctatttt atggaaacat tatatggtat tgccacggta       3000
aaaatccagg ggatggtcgg aattcggggg gcacactggc ttaatatgaa aatagatgcg       3060
ataaattcgg gtattaagct aaccaggatg gatttgctct tcggaggaat aaataccttt       3120
gttaccgcct gtgatcagat tgtaattttta tggctgggag caggccttgt gatcgataat       3180
```

```
cagatgacaa taggaatgtt tgtagcgttt agttcttttc gtgggcagtt ttcggaaaga    3240
gttgcctctc tgaccagttt tcttcttcag ctaagaataa tgagtctgca caatgagcgc    3300
attgcagata ttgcattaca tgaaaaggag gaaaagaaac ctgaaattga aatcgttgct    3360
gatatggggc caatatccct ggaaaccaat ggtttaagct atcgttatga cagtcagtca    3420
gcaccgatat tcagtgctct gagtttatct gtagctccgg gggaaagtgt ggctataact    3480
ggtgcttccg gtgcgggaaa aaccacatta atgaaagtac tatgtggact atttgaacct    3540
gatagcggga gggtactgat aaatggtata gatatacgcc aaattggaat aaataattat    3600
caccggatga tagcctgtgt tatgcaggat gaccggctat tttcaggctc aattcgtgaa    3660
aatatctgtg gttttgcaga ggaaatggat gaagagtgga tggtagaatg tgccagagca    3720
agtcatattc atgatgttat aatgaatatg ccaatgggat atgaaacatt aataggtgaa    3780
cttggggaag gtcttctctg cggtcaaaaa cagcgtatat ttattgcacg agccttatac    3840
cggaaaccag gaatattatt tatggatgag gcaaccagtg ctcttgattc agagagtgaa    3900
catttcgtga atgttgccat aaaaaacatg aatatcacca gggtaattat tgcacacaga    3960
gaaacaacgt tgagaactgt tgatagagtt atttctatt aaaccataga ggaattacaa    4020
gcgtatgagg aatatttctt cctgttataa ttcctcgtta tgctcagata tctgttggag    4080
gtggaatgga agatagacaa tccaccaaga agaaatatca ttctgtgtgg attgtccaat    4140
aactcgctgt cacgcttgag accacccctg cagtccggca aaaagggca aggtgtcacc    4200 accctgccct ttttctttaa aaccgaaaag attacttcgc gttatgcagg cttcctcgct    4260
cactgactcg ctgcgctcgg tcgttcggct gcggcgagcg gtatcagctc actcaaaggc    4320
ggtaatacgg ttatccacag aatcaggga taacgcagga agaacatgt gagcaaaagg    4380 ccagcaaaag gccaggaacc gtaaaaaggc cgcgttgctg gcgttttcc acaggctccg    4440 cccccctgac gagcatcaca aaatcgacg ctcaagtcag aggtggcgaa acccgacagg    4500
actataaaga taccaggcgt ttccccctgg aagctccctc gtgcgctctc ctgttccgac    4560
cctgccgctt accggatacc tgtccgcctt tctcccttcg ggaagcgtgg cgctttctca    4620
tagctcacgc tgtaggtatc tcagttcggt gtaggtcgtt cgctccaagc tgggctgtgt    4680
gcacgaaccc cccgttcagc ccgaccgctg cgccttatcc ggtaactatc gtcttgagtc    4740
caacccggta agacacgact tatcgccact ggcagcagcc actggtaaca ggattagcag    4800
agcgaggtat gtaggcggtg ctacagagtt cttgaagtgg tggcctaact acggctacac    4860
tagaagaaca gtatttggta tctgcgctct gctgaagcca gttaccttcg gaaaaagagt    4920
tggtagctct tgatccggca aacaaaccac cgctggtagc ggtggttttt tgtttgcaa    4980 gcagcagatt acgcgcagaa aaaaaggatc tcaagaagat cctttgatct tttctacggg    5040
gtctgacgct cagtggaacg aaaactcacg ttaagggatt ttggtcatga gattatcaaa    5100
aaggatcttc acctagatcc ttttaaatta aaaatgaagt tttaaatcaa tctaaagtat    5160
atatgagtaa acttggtctg acagctcgag gcttggattc tcaccaataa aaaacgcccg    5220
gcggcaaccg agcgttctga caaatccag atggagttct gaggtcatta ctggatctat    5280
caacaggagt ccaagcgagc tcgatatcaa attacgcccc gccctgccac tcatcgcagt    5340
actgttgtaa ttcattaagc attctgccga catggaagcc atcacaaacg gcatgatgaa    5400
cctgaatcgc cagcggcatc agcaccttgt cgccttgcgt ataatatttg cccatggtga    5460 aaacggggc gaagaagttg tccatattgg ccacgtttaa atcaaaactg gtgaaactca    5520
```

```
cccagggatt ggctgagacg aaaaacatat tctcaataaa cccttaggg aaataggcca    5580 ggttttcacc gtaacacgcc acatcttgcg aatatatgtg tagaaactgc cggaaatcgt    5640
cgtggtattc actccagagc gatgaaaacg tttcagtttg ctcatggaaa acggtgtaac    5700
aagggtgaac actatcccat atcaccagct caccgtcttt cattgccata cgaaattccg    5760
gatgagcatt catcaggcgg gcaagaatgt gaataaaggc cggataaaac ttgtgcttat    5820 ttttcttac ggtcttaaa aaggccgtaa tatccagctg aacggtctgg ttataggtac    5880
attgagcaac tgactgaaat gcctcaaaat gttctttacg atgccattgg gatatatcaa    5940
cggtggtata tccagtgatt ttttctcca tttagcttc cttagctcct gaaaatctcg    6000
ataactcaaa aaatacgccc ggtagtgatc ttatttcatt atggtgaaag ttggaacctc    6060
ttacgtgccc gatcaactcg agtgccacct gacgtctaag aaaccattat tatcatgaca    6120
ttaacctata aaataggcg t                                              6141
```

<210> SEQ ID NO 14
<211> LENGTH: 47
<212> TYPE: PRT
<213> ORGANISM: Enterococcus faecium

<400> SEQUENCE: 14

Thr Thr His Ser Gly Lys Tyr Tyr Gly Asn Gly Val Tyr Cys Thr Lys
1               5                   10                  15

Asn Lys Cys Thr Val Asp Trp Ala Lys Ala Thr Thr Cys Ile Ala Gly
            20                  25                  30

Met Ser Ile Gly Gly Phe Leu Gly Gly Ala Ile Pro Gly Lys Cys
        35                  40                  45

<210> SEQ ID NO 15
<211> LENGTH: 44
<212> TYPE: PRT
<213> ORGANISM: Enterococcus faecium

<400> SEQUENCE: 15

Ala Thr Arg Ser Tyr Gly Asn Gly Val Tyr Cys Asn Asn Ser Lys Cys
1               5                   10                  15

Trp Val Asn Trp Gly Glu Ala Lys Glu Asn Ile Ala Gly Ile Val Ile
            20                  25                  30

Ser Gly Trp Ala Ser Gly Leu Ala Gly Met Gly His
        35                  40

<210> SEQ ID NO 16
<211> LENGTH: 53
<212> TYPE: PRT
<213> ORGANISM: Enterococcus faecium

<400> SEQUENCE: 16

Glu Asn Asp His Arg Met Pro Asn Glu Leu Asn Arg Pro Asn Asn Leu
1               5                   10                  15

Ser Lys Gly Gly Ala Lys Cys Gly Ala Ala Ile Ala Gly Gly Leu Phe
            20                  25                  30

Gly Ile Pro Lys Gly Pro Leu Ala Trp Ala Ala Gly Leu Ala Asn Val
        35                  40                  45

Tyr Ser Lys Cys Asn
    50

<210> SEQ ID NO 17
<211> LENGTH: 44

```
<212> TYPE: PRT
<213> ORGANISM: Enterococcus hirae

<400> SEQUENCE: 17

Ala Thr Tyr Tyr Gly Asn Gly Leu Tyr Cys Asn Lys Glu Lys Cys Trp
1               5                   10                  15

Val Asp Trp Asn Gln Ala Lys Gly Glu Ile Gly Lys Ile Ile Val Asn
                20                  25                  30

Gly Trp Val Asn His Gly Pro Trp Ala Pro Arg Arg
            35                  40

<210> SEQ ID NO 18
<211> LENGTH: 289
<212> TYPE: PRT
<213> ORGANISM: Enterococcus faecalis

<400> SEQUENCE: 18

Met Ala Gly Glu Val Phe Ser Ser Leu Ile Thr Ser Val Asn Pro Asn
1               5                   10                  15

Pro Met Asn Ala Gly Ser Arg Asn Gly Ile Pro Ile Asp Thr Ile Ile
                20                  25                  30

Leu His His Asn Ala Thr Thr Asn Lys Asp Val Ala Met Asn Thr Trp
            35                  40                  45

Leu Leu Gly Gly Gly Ala Gly Thr Ser Ala His Tyr Glu Cys Thr Pro
50                  55                  60

Thr Glu Ile Ile Gly Cys Val Gly Glu Gln Tyr Ser Ala Phe His Ala
65                  70                  75                  80

Gly Gly Thr Gly Gly Ile Asp Val Pro Lys Ile Ala Asn Pro Asn Gln
                85                  90                  95

Arg Ser Ile Gly Ile Glu Asn Val Asn Ser Ser Gly Ala Pro Asn Trp
            100                 105                 110

Ser Val Asp Pro Arg Thr Ile Thr Asn Cys Ala Arg Leu Val Ala Asp
        115                 120                 125

Ile Cys Thr Arg Tyr Gly Ile Pro Cys Asp Arg Gln His Val Leu Gly
130                 135                 140

His Asn Glu Val Thr Ala Thr Cys Pro Gly Gly Met Asp Val Asp
145                 150                 155                 160

Glu Val Val Arg Gln Ala Gln Gln Phe Met Ala Gly Gly Ser Asn Asn
                165                 170                 175

Ala Val Lys Pro Glu Pro Ser Lys Pro Thr Pro Ser Lys Pro Ser Asn
            180                 185                 190

Asn Lys Asn Lys Glu Gly Val Ala Thr Met Tyr Cys Leu Tyr Glu Arg
        195                 200                 205

Pro Ile Asn Ser Lys Thr Gly Val Leu Glu Trp Asn Gly Asp Ala Trp
210                 215                 220

Thr Val Met Phe Cys Asn Gly Val Asn Cys Arg Arg Val Ser His Pro
225                 230                 235                 240

Asp Glu Met Lys Val Ile Glu Asp Ile Tyr Arg Lys Asn Asn Gly Lys
                245                 250                 255

Asp Ile Pro Phe Tyr Ser Gln Lys Glu Trp Asn Lys Asn Ala Pro Trp
            260                 265                 270

Tyr Asn Arg Leu Glu Thr Val Cys Pro Val Val Gly Ile Thr Lys Lys
        275                 280                 285

Ser
```

```
<210> SEQ ID NO 19
<211> LENGTH: 410
<212> TYPE: PRT
<213> ORGANISM: Bacteriophage f1

<400> SEQUENCE: 19

Met Ser Asn Ile Asn Met Glu Thr Ala Ile Ala Asn Met Tyr Ala Leu
1               5                   10                  15

Lys Ala Arg Gly Ile Thr Tyr Ser Met Asn Tyr Ser Arg Thr Gly Ala
            20                  25                  30

Asp Gly Thr Gly Asp Cys Ser Gly Thr Val Tyr Asp Ser Leu Arg Lys
        35                  40                  45

Ala Gly Ala Ser Asp Ala Gly Trp Val Leu Asn Thr Asp Ser Met His
    50                  55                  60

Ser Trp Leu Glu Lys Asn Gly Phe Lys Leu Ile Ala Gln Asn Lys Glu
65                  70                  75                  80

Trp Ser Ala Lys Arg Gly Asp Val Val Ile Phe Gly Lys Lys Gly Ala
                85                  90                  95

Ser Gly Gly Ser Ala Gly His Val Val Ile Phe Ile Ser Ser Thr Gln
            100                 105                 110

Ile Ile His Cys Thr Trp Lys Ser Ala Thr Ala Asn Gly Val Tyr Val
        115                 120                 125

Asp Asn Glu Ala Thr Thr Cys Pro Tyr Ser Met Gly Trp Tyr Val Tyr
    130                 135                 140

Arg Leu Asn Gly Gly Ser Thr Pro Pro Lys Pro Asn Thr Lys Lys Val
145                 150                 155                 160

Lys Val Leu Lys His Ala Thr Asn Trp Ser Pro Ser Lys Gly Ala
                165                 170                 175

Lys Met Ala Ser Phe Val Lys Gly Gly Thr Phe Glu Val Lys Gln Gln
            180                 185                 190

Arg Pro Ile Ser Tyr Ser Tyr Ser Asn Gln Glu Tyr Leu Ile Val Asn
        195                 200                 205

Lys Gly Thr Val Leu Gly Trp Val Leu Ser Gln Asp Ile Glu Gly Gly
    210                 215                 220

Tyr Gly Ser Asp Arg Val Gly Gly Ser Lys Pro Lys Leu Pro Ala Gly
225                 230                 235                 240

Phe Thr Lys Glu Glu Ala Thr Phe Ile Asn Gly Asn Ala Pro Ile Thr
                245                 250                 255

Thr Arg Lys Asn Lys Pro Ser Leu Ser Ser Gln Thr Ala Thr Pro Leu
            260                 265                 270

Tyr Pro Gly Gln Ser Val Arg Tyr Leu Gly Trp Lys Ser Ala Glu Gly
        275                 280                 285

Tyr Ile Trp Ile Tyr Ala Thr Asp Gly Arg Tyr Ile Pro Val Arg Pro
    290                 295                 300

Val Gly Lys Glu Ala Trp Gly Thr Phe Lys Gln Asp Ile Glu Gly Gly
305                 310                 315                 320

Tyr Gly Ser Asp Arg Val Gly Gly Ser Lys Pro Lys Leu Pro Ala Gly
                325                 330                 335

Phe Thr Lys Glu Glu Ala Thr Phe Ile Asn Gly Asn Ala Pro Ile Thr
            340                 345                 350

Thr Arg Lys Asn Lys Pro Ser Leu Ser Ser Gln Thr Ala Thr Pro Leu
        355                 360                 365

Tyr Pro Gly Gln Ser Val Arg Tyr Leu Gly Trp Lys Ser Ala Glu Gly
    370                 375                 380
```

```
Tyr Ile Trp Ile Tyr Ala Thr Asp Gly Arg Tyr Ile Pro Val Arg Pro
385                 390                 395                 400

Val Gly Lys Glu Ala Trp Gly Thr Phe Lys
            405                 410

<210> SEQ ID NO 20
<211> LENGTH: 328
<212> TYPE: PRT
<213> ORGANISM: Bacteriophage EFAP-1

<400> SEQUENCE: 20

Met Lys Leu Lys Gly Ile Leu Leu Ser Val Val Thr Thr Phe Gly Leu
1               5                   10                  15

Leu Phe Gly Ala Thr Asn Val Gln Ala Tyr Glu Val Asn Asn Glu Phe
            20                  25                  30

Asn Leu Gln Pro Trp Glu Gly Ser Gln Gln Leu Ala Tyr Pro Asn Lys
        35                  40                  45

Ile Ile Leu His Glu Thr Ala Asn Pro Arg Ala Thr Gly Arg Asn Glu
50                  55                  60

Ala Thr Tyr Met Lys Asn Asn Trp Phe Asn Ala His Thr Thr Ala Ile
65                  70                  75                  80

Val Gly Asp Gly Gly Ile Val Tyr Lys Val Ala Pro Glu Gly Asn Val
                85                  90                  95

Ser Trp Gly Ala Gly Asn Ala Asn Pro Tyr Ala Pro Val Gln Ile Glu
            100                 105                 110

Leu Gln His Thr Asn Asp Pro Glu Leu Phe Lys Ala Asn Tyr Lys Ala
        115                 120                 125

Tyr Val Asp Tyr Thr Arg Asp Met Gly Lys Lys Phe Gly Ile Pro Met
130                 135                 140

Thr Leu Asp Gln Gly Gly Ser Leu Trp Glu Lys Gly Val Val Ser His
145                 150                 155                 160

Gln Trp Val Thr Asp Phe Val Trp Gly Asp His Thr Asp Pro Tyr Gly
                165                 170                 175

Tyr Leu Ala Lys Met Gly Ile Ser Lys Ala Gln Leu Ala His Asp Leu
            180                 185                 190

Ala Asn Gly Val Ser Gly Asn Thr Ala Thr Pro Thr Pro Lys Pro Asp
        195                 200                 205

Lys Pro Lys Pro Thr Gln Pro Ser Lys Pro Ser Asn Lys Lys Arg Phe
210                 215                 220

Asn Tyr Arg Val Asp Gly Leu Glu Tyr Val Asn Gly Met Trp Gln Ile
225                 230                 235                 240

Tyr Asn Glu His Leu Gly Lys Ile Asp Phe Asn Trp Thr Glu Asn Gly
                245                 250                 255

Ile Pro Val Glu Val Val Asp Lys Val Asn Pro Ala Thr Gly Gln Pro
            260                 265                 270

Thr Lys Asp Gln Val Leu Lys Val Gly Asp Tyr Phe Asn Phe Gln Glu
        275                 280                 285

Asn Ser Thr Gly Val Val Gln Glu Gln Thr Pro Tyr Met Gly Tyr Thr
290                 295                 300

Leu Ser His Val Gln Leu Pro Asn Glu Phe Ile Trp Leu Phe Thr Asp
305                 310                 315                 320

Ser Lys Gln Ala Leu Met Tyr Gln
            325

<210> SEQ ID NO 21
```

```
<211> LENGTH: 289
<212> TYPE: PRT
<213> ORGANISM: Bacteriophage jEF24C

<400> SEQUENCE: 21

Met Ala Gly Glu Val Phe Ser Ser Leu Ile Thr Ser Val Asn Pro Asn
1               5                   10                  15

Pro Met Asn Ala Gly Ser Arg Asn Gly Ile Pro Ile Asp Thr Ile Ile
                20                  25                  30

Leu His His Asn Ala Thr Thr Asn Lys Asp Val Ala Met Asn Thr Trp
            35                  40                  45

Leu Leu Gly Gly Gly Ala Gly Thr Ser Ala His Tyr Glu Cys Thr Pro
50                  55                  60

Thr Glu Ile Ile Gly Cys Val Gly Glu Gln Tyr Ser Ala Phe His Ala
65                  70                  75                  80

Gly Gly Thr Gly Gly Ile Asp Val Pro Lys Ile Ala Asn Pro Asn Gln
                85                  90                  95

Arg Ser Ile Gly Ile Glu Asn Val Asn Ser Ser Gly Ala Pro Asn Trp
            100                 105                 110

Ser Val Asp Pro Arg Thr Ile Thr Asn Cys Ala Arg Leu Val Ala Asp
        115                 120                 125

Ile Cys Thr Arg Tyr Gly Ile Pro Cys Asp Arg Gln His Val Leu Gly
130                 135                 140

His Asn Glu Val Thr Ala Thr Ala Cys Pro Gly Gly Met Asp Val Asp
145                 150                 155                 160

Glu Val Val Arg Gln Ala Gln Gln Phe Met Ala Gly Gly Ser Asn Asn
                165                 170                 175

Ala Val Lys Pro Glu Pro Ser Lys Pro Thr Pro Ser Lys Pro Ser Asn
            180                 185                 190

Asn Lys Asn Lys Glu Gly Val Ala Thr Met Tyr Cys Leu Tyr Glu Arg
        195                 200                 205

Pro Ile Asn Ser Lys Thr Gly Val Leu Glu Trp Asn Gly Asp Ala Trp
210                 215                 220

Thr Val Met Phe Cys Asn Gly Val Asn Cys Arg Arg Val Ser His Pro
225                 230                 235                 240

Asp Glu Met Lys Val Ile Glu Asp Ile Tyr Arg Lys Asn Asn Gly Lys
                245                 250                 255

Asp Ile Pro Phe Tyr Ser Gln Lys Glu Trp Asn Lys Asn Ala Pro Trp
            260                 265                 270

Tyr Asn Arg Leu Glu Thr Val Cys Pro Val Val Gly Ile Thr Lys Lys
        275                 280                 285

Ser

<210> SEQ ID NO 22
<211> LENGTH: 237
<212> TYPE: PRT
<213> ORGANISM: Bacteriophage F168/08

<400> SEQUENCE: 22

Met Val Lys Leu Asn Asp Val Leu Ser Tyr Val Asn Gly Leu Val Gly
1               5                   10                  15

Lys Gly Val Asp Ala Asp Gly Trp Tyr Gly Thr Gln Cys Met Asp Leu
                20                  25                  30

Thr Val Asp Val Met Gln Arg Phe Phe Gly Trp Arg Pro Tyr Gly Asn
            35                  40                  45
```

```
Ala Ile Ala Leu Val Asp Gln Pro Ile Pro Ala Gly Phe Gln Arg Ile
 50                  55                  60

Arg Thr Thr Ser Ser Thr Gln Ile Lys Ala Gly Asp Val Met Ile Trp
 65                  70                  75                  80

Gly Leu Gly Tyr Tyr Ala Gln Tyr Gly His Thr His Ile Ala Thr Glu
                 85                  90                  95

Asp Gly Arg Ala Asp Gly Thr Phe Val Ser Val Asp Gln Asn Trp Ile
            100                 105                 110

Asn Pro Ser Leu Glu Val Gly Ser Pro Ala Ala Ile His His Asn
        115                 120                 125

Met Asp Gly Val Trp Val Ile Arg Pro Pro Tyr Glu Ala Glu Ser
130                 135                 140

Lys Pro Lys Pro Pro Ala Pro Lys Pro Asp Lys Pro Asn Leu Gly Gln
145                 150                 155                 160

Phe Lys Gly Asp Asp Asp Ile Met Phe Ile Tyr Tyr Lys Lys Thr Lys
                165                 170                 175

Gln Gly Ser Thr Glu Gln Trp Phe Val Ile Gly Gly Lys Arg Ile Tyr
            180                 185                 190

Leu Pro Thr Met Thr Tyr Val Asn Glu Ala Asn Asp Leu Ile Lys Arg
        195                 200                 205

Tyr Gly Gly Asn Thr Asn Val Thr Thr Tyr Asn Tyr Asp Asn Phe Gly
210                 215                 220

Leu Ala Met Met Glu Lys Ala Tyr Pro Gln Val Lys Leu
225                 230                 235

<210> SEQ ID NO 23
<211> LENGTH: 25
<212> TYPE: PRT
<213> ORGANISM: Lactobacillus plantarum

<400> SEQUENCE: 23

Gly Ala Trp Lys Asn Phe Trp Ser Ser Leu Arg Lys Gly Phe Tyr Asp
 1               5                  10                  15

Gly Glu Ala Gly Arg Ala Ile Arg Arg
             20                  25

<210> SEQ ID NO 24
<211> LENGTH: 32
<212> TYPE: PRT
<213> ORGANISM: Lactobacillus plantarum

<400> SEQUENCE: 24

Arg Arg Ser Arg Lys Asn Gly Ile Gly Tyr Ala Ile Gly Tyr Ala Phe
 1               5                  10                  15

Gly Ala Val Glu Arg Ala Val Leu Gly Gly Ser Arg Asp Tyr Asn Lys
             20                  25                  30

<210> SEQ ID NO 25
<211> LENGTH: 33
<212> TYPE: PRT
<213> ORGANISM: Lactobacillus plantarum

<400> SEQUENCE: 25

Phe Asn Arg Gly Gly Tyr Asn Phe Gly Lys Ser Val Arg His Val Val
 1               5                  10                  15

Asp Ala Ile Gly Ser Val Ala Gly Ile Arg Gly Ile Leu Lys Ser Ile
             20                  25                  30

Arg
```

```
<210> SEQ ID NO 26
<211> LENGTH: 34
<212> TYPE: PRT
<213> ORGANISM: Lactobacillus plantarum

<400> SEQUENCE: 26

Val Phe His Ala Tyr Ser Ala Arg Gly Val Arg Asn Asn Tyr Lys Ser
 1               5                  10                  15

Ala Val Gly Pro Ala Asp Trp Val Ile Ser Ala Val Arg Gly Phe Ile
            20                  25                  30

His Gly

<210> SEQ ID NO 27
<211> LENGTH: 75
<212> TYPE: PRT
<213> ORGANISM: Escherichia coli

<400> SEQUENCE: 27

Ala Gly Asp Pro Leu Ala Asp Pro Asn Ser Gln Ile Val Arg Gln Ile
 1               5                  10                  15

Met Ser Asn Ala Ala Trp Gly Ala Ala Phe Gly Ala Arg Gly Gly Leu
            20                  25                  30

Gly Gly Met Ala Val Gly Ala Ala Gly Val Thr Gln Thr Val Leu
         35                  40                  45

Gln Gly Ala Ala Ala His Met Pro Val Asn Val Pro Ile Pro Lys Val
     50                  55                  60

Pro Met Gly Pro Ser Trp Asn Gly Ser Lys Gly
 65                  70                  75

<210> SEQ ID NO 28
<211> LENGTH: 19
<212> TYPE: DNA
<213> ORGANISM: Escherichia coli

<400> SEQUENCE: 28
gatcgcccga acagcaatg                                         19

<210> SEQ ID NO 29
<211> LENGTH: 23
<212> TYPE: DNA
<213> ORGANISM: Escherichia coli

<400> SEQUENCE: 29
ataaaaaagt aggatttatc cgc                                    23

<210> SEQ ID NO 30
<211> LENGTH: 27
<212> TYPE: DNA
<213> ORGANISM: Escherichia coli

<400> SEQUENCE: 30
tcaagtacta atagtgatat tttaagg                                27

<210> SEQ ID NO 31
<211> LENGTH: 27
<212> TYPE: DNA
<213> ORGANISM: Escherichia coli

<400> SEQUENCE: 31
ttaaaaaagt aggatttatc gataaag                                27
```

```
<210> SEQ ID NO 32
<211> LENGTH: 21
<212> TYPE: DNA
<213> ORGANISM: Escherichia coli

<400> SEQUENCE: 32
cacacacaaa cgggagctgt t                                              21

<210> SEQ ID NO 33
<211> LENGTH: 21
<212> TYPE: DNA
<213> ORGANISM: Escherichia coli

<400> SEQUENCE: 33
cttcccgcag catagttcca t                                              21

<210> SEQ ID NO 34
<211> LENGTH: 22
<212> TYPE: DNA
<213> ORGANISM: Escherichia coli

<400> SEQUENCE: 34
aagtcaaagc aggggttgcc cg                                             22

<210> SEQ ID NO 35
<211> LENGTH: 21
<212> TYPE: DNA
<213> ORGANISM: Escherichia coli

<400> SEQUENCE: 35
gacgccgaca ttaagacgca g                                              21

<210> SEQ ID NO 36
<211> LENGTH: 28
<212> TYPE: DNA
<213> ORGANISM: Escherichia coli

<400> SEQUENCE: 36
tcatcccgga agcctccctc actactat                                       28

<210> SEQ ID NO 37
<211> LENGTH: 28
<212> TYPE: DNA
<213> ORGANISM: Escherichia coli

<400> SEQUENCE: 37
tagcgtttgc tgcactggct tctgatac                                       28

<210> SEQ ID NO 38
<211> LENGTH: 24
<212> TYPE: DNA
<213> ORGANISM: Escherichia coli

<400> SEQUENCE: 38
ggcgatttag gcattccgat actc                                           24

<210> SEQ ID NO 39
<211> LENGTH: 20
<212> TYPE: DNA
<213> ORGANISM: Escherichia coli

<400> SEQUENCE: 39
```
acggggtcgc tagttaagga                                                  20

<210> SEQ ID NO 40
<211> LENGTH: 26
<212> TYPE: DNA
<213> ORGANISM: Escherichia coli

<400> SEQUENCE: 40
cagcagcgct tcggacaaaa tctcct                                           26

<210> SEQ ID NO 41
<211> LENGTH: 26
<212> TYPE: DNA
<213> ORGANISM: Escherichia coli

<400> SEQUENCE: 41
ttccccacca ctctccgttc tcaaac                                           26

<210> SEQ ID NO 42
<211> LENGTH: 22
<212> TYPE: DNA
<213> ORGANISM: Escherichia coli

<400> SEQUENCE: 42
cagcaacccg aaccacttga tg                                               22

<210> SEQ ID NO 43
<211> LENGTH: 21
<212> TYPE: DNA
<213> ORGANISM: Escherichia coli

<400> SEQUENCE: 43
agcattgcca gagcggcaga a                                                21

<210> SEQ ID NO 44
<211> LENGTH: 22
<212> TYPE: DNA
<213> ORGANISM: Escherichia coli

<400> SEQUENCE: 44
ggctggacat catgggaact gg                                               22

<210> SEQ ID NO 45
<211> LENGTH: 21
<212> TYPE: DNA
<213> ORGANISM: Escherichia coli

<400> SEQUENCE: 45
cgtcgggaac gggtagaatc g                                                21

<210> SEQ ID NO 46
<211> LENGTH: 20
<212> TYPE: DNA
<213> ORGANISM: Escherichia coli

<400> SEQUENCE: 46
gatgactcag ccacgggtaa                                                  20

<210> SEQ ID NO 47
<211> LENGTH: 20
<212> TYPE: DNA
<213> ORGANISM: Escherichia coli

<400> SEQUENCE: 47

```
ccaggactca cctcacgaat                                                    20

<210> SEQ ID NO 48
<211> LENGTH: 25
<212> TYPE: DNA
<213> ORGANISM: Escherichia coli

<400> SEQUENCE: 48
gtggcagtat gagtaatgac cgtta                                              25

<210> SEQ ID NO 49
<211> LENGTH: 25
<212> TYPE: DNA
<213> ORGANISM: Escherichia coli

<400> SEQUENCE: 49
atatcctttc tgcagggatg caata                                              25

<210> SEQ ID NO 50
<211> LENGTH: 7
<212> TYPE: PRT
<213> ORGANISM: Artificial Sequence
<220> FEATURE:
<223> OTHER INFORMATION: Class IIa bacteriocin N-terminal consensus
      sequence
<220> FEATURE:
<221> NAME/KEY: MISC_FEATURE
<222> LOCATION: (5)..(5)
<223> OTHER INFORMATION: Xaa can be Valine or Lysine
<220> FEATURE:
<221> NAME/KEY: MISC_FEATURE
<222> LOCATION: (6)..(6)
<223> OTHER INFORMATION: Xaa can be any naturally occurring amino acid.

<400> SEQUENCE: 50

Tyr Gly Asn Gly Xaa Xaa Cys
1               5
```